(12) United States Patent
Zhang

(10) Patent No.: US 11,723,961 B2
(45) Date of Patent: Aug. 15, 2023

(54) MASPIN, MASPIN DERIVATIVES, AND MASPIN MIMETICS FOR REDUCING ROS, INFLAMMATION, AND SKIN AGING

(71) Applicant: Northwestern University, Evanston, IL (US)

(72) Inventor: Ming Zhang, Chicago, IL (US)

(73) Assignee: Northwestern University, Evanston, IL (US)

( * ) Notice: Subject to any disclaimer, the term of this patent is extended or adjusted under 35 U.S.C. 154(b) by 0 days.

(21) Appl. No.: 17/383,597

(22) Filed: Jul. 23, 2021

(65) Prior Publication Data

US 2021/0346474 A1    Nov. 11, 2021

Related U.S. Application Data

(63) Continuation of application No. 16/739,930, filed on Jan. 10, 2020, now abandoned, which is a continuation of application No. 16/104,751, filed on Aug. 17, 2018, now abandoned, which is a continuation of application No. 14/945,882, filed on Nov. 19, 2015, now abandoned.

(60) Provisional application No. 62/082,456, filed on Nov. 20, 2014.

(51) Int. Cl.
| | | |
|---|---|---|
| *A61K 38/57* | (2006.01) | |
| *A61K 8/64* | (2006.01) | |
| *A61Q 19/08* | (2006.01) | |
| *A61K 9/00* | (2006.01) | |

(52) U.S. Cl.
CPC ............... *A61K 38/57* (2013.01); *A61K 8/64* (2013.01); *A61K 9/0014* (2013.01); *A61Q 19/08* (2013.01); *A61K 2800/782* (2013.01)

(58) Field of Classification Search
CPC ........ A61K 38/57; A61K 8/64; A61K 9/0014; A61K 2800/782; A61Q 19/08
See application file for complete search history.

(56) References Cited

U.S. PATENT DOCUMENTS

| | | |
|---|---|---|
| 2012/0302506 A1 | 11/2012 | Zhang |
| 2016/0144006 A1 | 5/2016 | Zhang |
| 2018/0353579 A1 | 12/2018 | Zhang |

OTHER PUBLICATIONS

Mahajan et al, Tumor-suppressive Maspin Functions as a Reactive Oxygen Species Scavenger, The Journal of Biological Chemistry, 2013, 288, pp. 11611-11620.*
Abdali et al., How effective are antioxidant supplements in obesity and diabetes? Med Princ Pract. 2015;24(3):201-15.
Aghajanian et al., Direct activation of RhoA by reactive oxygen species requires a redox-sensitive motif. PLoS One. Nov. 26, 2009;4(11):e8045.
Al-Ayyoubi et al., Crystal structure of human maspin, a serpin with antitumor properties: reactive center loop of maspin is exposed but constrained. J Biol Chem. Dec. 31, 2004;279(53):55540-4.
Alfadda et al. Reactive oxygen species in health and disease. J Biomed Biotechnol. 2012;2012:936486.
Bailey et al., Biological functions of maspin. J Cell Physiol. Dec. 2006;209(3):617-24.
Bailey et al., Mammary serine protease inhibitor (Maspin) binds directly to interferon regulatory factor 6: identification of a novel serpin partnership. J Biol Chem. Oct. 7, 2005;280(40):34210-7.
Baldock et al., Shape of tropoelastin, the highly extensible protein that controls human tissue elasticity. PNAS. 2011;108(11):4322-27.
Balmus et al., The implications of oxidative stress and antioxidant therapies in Inflammatory Bowel Disease: Clinical aspects and animal models. Saudi J Gastroenterol. Jan.-Feb. 2016;22(1):3-17.
Berendsen et al., A glimpse of the Holy Grail? Science. Oct. 23, 1998;282(5389):642-3.
Bodenstine et al., Maspin: molecular mechanisms and therapeutic implications. Cancer Metastasis Rev. Dec. 2012;31(3-4):529-51.
Bradley et al., Limits of cooperativity in a structurally modular protein: response of the Notch ankyrin domain to analogous alanine substitutions in each repeat. J Mol Biol. Nov. 22, 2002;324(2):373-86.
Brieger et al., Reactive oxygen species: from health to disease. Swiss Med Wkly. Aug. 17, 2012;142:w13659.
Brown et al., Protein scaffolds in MAP kinase signalling. Cell Signal. Apr. 2009;21(4):462-9.
Cai et al., Mammary serine protease inhibitor inhibits epithelial growth factor-induced epithelial-mesenchymal transition of esophageal carcinoma cells. Cancer. Jan. 1, 2009;115(1):36-48.
Cella et al., Maspin is physically associated with [beta]1 integrin regulating cell adhesion in mammary epithelial cells. FASEB J. Jul. 2006;20(9):1510-2.
Charles et al., Protein sulfenation as a redox sensor: proteomics studies using a novel biotinylated dimedone analogue. Mol Cell Proteomics. Sep. 2007;6(9):1473-84.
Corbett et al., Changes in cell spreading and cytoskeletal organization are induced by adhesion to a fibronectin-fibrin matrix. Blood. Jul. 1, 1996;88(1):158-66.
Dalle-Donne et al., Biomarkers of oxidative damage in human disease. Clin Chem. Apr. 2006;52(4):601-23.
Danielson et al., Epithelial mouse mammary cell line exhibiting normal morphogenesis in vivo and functional differentiation in vitro. Proc Natl Acad Sci USA. Jun. 1984;81(12):3756-60.

(Continued)

*Primary Examiner* — Li N Komatsu
(74) *Attorney, Agent, or Firm* — Casimir Jones, S.C.; Jason R. Bond

(57) ABSTRACT

The present invention provides compositions, methods, and systems for treating inflammatory conditions (e.g., by inhibiting reactive oxygen species) in or on a subject with maspin, maspin derivatives, or maspin mimetics. In some embodiments, such agents are applied to the skin of a subject (e.g., to reduce skin aging).

20 Claims, 12 Drawing Sheets

Specification includes a Sequence Listing.

(56) References Cited

OTHER PUBLICATIONS

Drumm et al. Genetic Variation and Clinical Heterogeneity in Cystic Fibrosis, Annu. Rev. Pathol. Mech. Dis., Jul. 2012, pp. 267-282.

Duan et al., MnSOD up-regulates maspin tumor suppressor gene expression in human breast and prostate cancer cells. Antioxid Redox Signal. Oct. 2003;5(5):677-88.

Endsley et al., Maspin, the molecular bridge between the plasminogen activator system and beta1 integrin that facilitates cell adhesion. J Biol Chem. Jul. 15, 2011;286(28):24599-607.

Eruslanov et al., Identification of ROS using oxidized DCFDA and flow-cytometry. Methods Mol Biol. 2010;594:57-72.

Ganceviciene et al., Skin anti-aging strategies. Dermatoendocrinol. Jul. 1, 2012;4(3):308-19.

Gao et al., Maspin plays an essential role in early embryonic development. Development. Apr. 2004;131(7):1479-89.

Golbidi et al., Antioxidants in the treatment of diabetes. Curr Diabetes Rev. Mar. 2011;7(2):106-25.

Gorouhi et al. 101 Topical Peptides and Proteins for Aging Skin, from M.A. Farage, K.W. Miller, H.I. Maibach (eds.), Textbook of Aging Skin, 2010, pp. 1089-1117.

Goszcz et al., Antioxidants in Cardiovascular Therapy: Panacea or False Hope? Front Cardiovasc Med. Jul. 6, 2015;2:29.

Hoffman et al., Oxygen sensitivity of mitochondrial reactive oxygen species generation depends on metabolic conditions. J Biol Chem. Jun. 12, 2009;284(24):16236-45.

ILIC et al., Lycopene for the prevention and treatment of benign prostatic hyperplasia and prostate cancer: a systematic review. Maturitas. Aug. 2012;72(4):269-76.

Jiang et al., Maspin sensitizes breast carcinoma cells to induced apoptosis. Oncogene. Jun. 13, 2002;21(26):4089-98.

Khandrika et al., Oxidative stress in prostate cancer. Cancer Lett. Sep. 18, 2009;282(2):125-36.

Kircik et al., Formulation Development, Testing, and Approval, Part 1 of 2, Practical Dermatology, 2010, pp. 1-16.

Klomsiri et al., Use of dimedone-based chemical probes for sulfenic acid detection evaluation of conditions affecting probe incorporation into redox-sensitive proteins. Methods Enzymol. 2010;473:77-94.

Krohn et al., Staurosporine-induced apoptosis of cultured rat hippocampal neurons involves caspase-1-like proteases as upstream initiators and increased production of superoxide as a main downstream effector. J Neurosci. Oct. 15, 1998;18(20):8186-97.

Kulinskii et al., Glutathione system. 1. Synthesis, transport, glutathione transferases, glutathione peroxidases. Biomed Khim. May-Jun. 2009;55(3):255-77.

Lane, Skin Penetration Enhancers. Intl J Pharma. 2013;447:12-21.

Law et al., The high resolution crystal structure of the human tumor suppressor maspin reveals a novel conformational switch in the G-helix. J Biol Chem. Jun. 10, 2005;280(23):22356-64.

Li et al., Maspin gene expression in tumor suppression induced by overexpressing manganese-containing superoxide dismutase cDNA in human breast cancer cells. Carcinogenesis. May 1998;19(5):833-9.

Li et al., Targeted expression of maspin in tumor vasculatures induces endothelial cell apoptosis. Oncogene. Mar. 17, 2005;24(12):2008-19.

Meng et al., Reversible oxidation and inactivation of protein tyrosine phosphatases in vivo. Mol Cell. Feb. 2002;9(2):387-99.

Minciullo et al., Oxidative stress in benign prostatic hyperplasia: a systematic review. Urol Int. 2015;94(3):249-54.

Mitta et al., Reactive oxygen species in inflammation and tissue injury. Antioxid Redox Signal. Mar. 1, 2014;20(7):1126-67.

Moura et al., Antioxidant therapy for treatment of inflammatory bowel disease: Does it work? Redox Biol. Dec. 2015;6:617-39.

Nasto, Biotech at the Beauty Counter. Nat. Biotech. 2007;25:617-19.

Nawata et al., Evidence of post-translational modification of the tumor suppressor maspin under oxidative stress. Int J Mol Med. Feb. 2011;27(2):249-54.

Nelson et al., Use of dimedone-based chemical probes for sulfenic acid detection methods to visualize and identify labeled proteins. Methods Enzymol. 2010;473:95-115.

Ngo et al., Computational Complexity, Protein Structure Predication and the Levinthal Paradox. In The Protein Folding Problem and Tertiary Structure Prediction. Merz and Le Grand Eds., 1994;pp. 491-494.

Pong et al., Attenuation of staurosporine-induced apoptosis, oxidative stress, and mitochondrial dysfunction by synthetic superoxide dismutase and catalase mimetics, in cultured cortical neurons. Exp Neurol. Sep. 2001;171(1):84-97.

Poole et al., Discovering mechanisms of signaling-mediated cysteine oxidation. Curr Opin Chem Biol. Feb. 2008;12(1):18-24.

Poole et al., Protein sulfenic acids in redox signaling. Annu Rev Pharmacol Toxicol. 2004;44:325-47.

Qin et al., Maspin regulates endothelial cell adhesion and migration through an integrin signaling pathway. J Biol Chem. Oct. 15, 2010;285(42):32360-9.

Reddy et al., Maspin expression inversely correlates with breast tumor progression in MMTV/TGF-alpha transgenic mouse model. Oncogene. Oct. 4, 2001;20(45):6538-43.

Rittle et al. UV-light-included signal cascades and skin aging, Ageing Research Reviews, 2002, 1, pp. 705-720.

Rudinger, Peptide Hormones. JA Parsons, ed., 1976, pp. 1-7.

Sabherwal et al., PDEF downregulates stathmin expression in prostate cancer. Int J Oncol. Jun. 2012;40(6):1889-99.

Seo et al., Profiling protein thiol oxidation in tumor cells using sulfenic acid-specific antibodies. Proc Natl Acad Sci USA. Sep. 22, 2009;106(38):16163-8.

Serru et al., Quantification of reduced and oxidized glutathione in whole blood samples by capillary electrophoresis. Clin Chem. 2001;47(7):1321-4.

Shi et al., Blocking tumor growth, invasion, and metastasis by maspin in a syngeneic breast cancer model. Cancer Res. Sep. 15, 2001;61(18):6945-51.

Shi et al., Maspin controls mammary tumor cell migration through inhibiting Rac1 and Cdc42, but not the RhoA GTPase. Cell Motil Cytoskeleton. May 2007;64(5):338-46.

Sigma, Custome Peptide Syntheis, Designing Custom Peptides, Technical Bulletin. 2004, 2 pages.

Trommer et al., Overcoming the Stratum Corneum: The Modulation of Skin Penetration. Skin Pharmacol Physiol. 2006;19:106-121.

Voet et al., Biochemistry, 2nd Edition, 1995; pp. 235-241.

Wang et al., Redox sensing by proteins: oxidative modifications on cysteines and the consequent events. Antioxid Redox Signal. Apr. 1, 2012;16(7):649-57.

Weinberg et al., Reactive oxygen species-dependent signaling regulates cancer. Cell Mol Life Sci. Dec. 2009;66(23):3663-73.

Xiao et al., Use of proteomics to demonstrate a hierarchical oxidative stress response to diesel exhaust particle chemicals in a macrophage cell line. J Biol Chem. Dec. 12, 2003;278(50):50781-90.

Yampolsky et al. The Exchangeability of Amino Acids in Proteins, Genetics, 2005, 170, pp. 1459-1472.

Yin et al., Tumor-suppressive maspin regulates cell response to oxidative stress by direct interaction with glutathione S-transferase. J Biol Chem. Oct. 14, 2005;280(41):34985-96.

Zhang et al., Maspin is an angiogenesis inhibitor. Nat Med. Feb. 2000;6(2):196-9.

Zhang et al., Maspin overexpression modulates tumor cell apoptosis through the regulation of Bcl-2 family proteins. BMC Cancer. May 20, 2005;5:50.

Zielonka et al., Hydroethidine- and MitoSOX-derived red fluorescence is not a reliable indicator of intracellular superoxide formation: another inconvenient truth. Free Radic Biol Med. Apr. 15, 2010;48(8):983-1001.

Zou et al., Maspin, a serpin with tumor-suppressing activity in human mammary epithelial cells. Science. Jan. 28, 1994;263(5146):526-9.

Chirani et al. History and Applications of Hydrogels, J Biomedical Sci., 2016, 4, pp. 1-23.

(56) References Cited

OTHER PUBLICATIONS

Amin et al. Hydrogels as potential drug delivery systems, Scientific Research and Essay, 2009, 3, pp. 1175-1183.

* cited by examiner

FIG. 1A
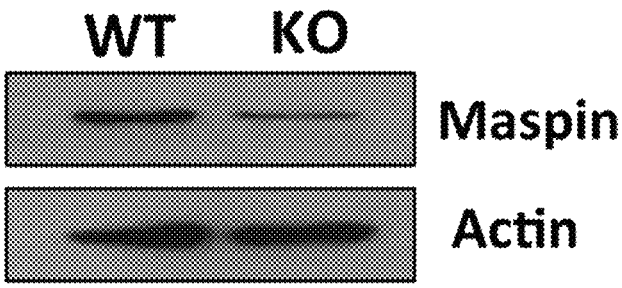
FIG. 1B
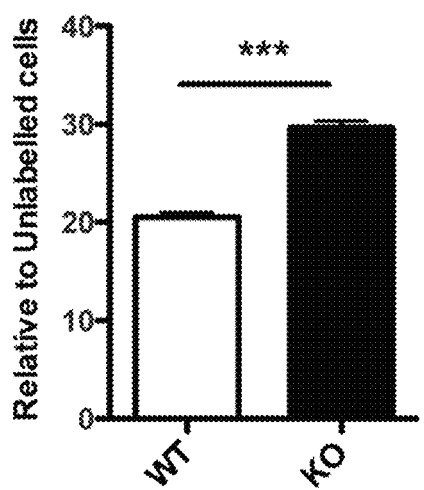
FIG. 1C
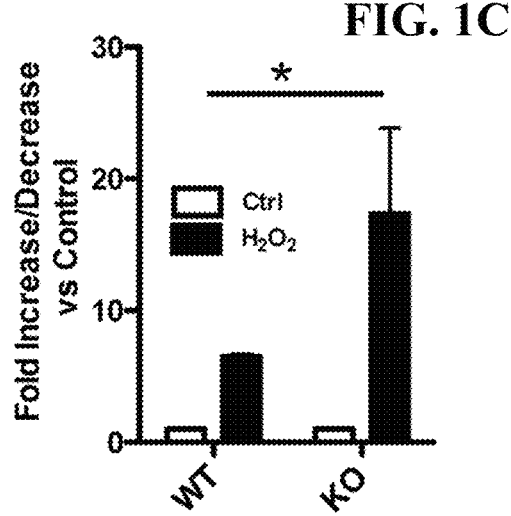
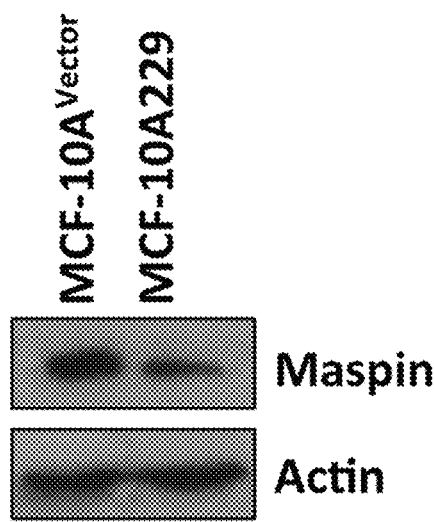
FIG. 1D
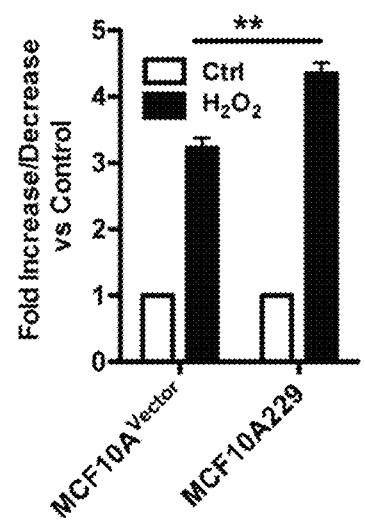
FIG. 1E

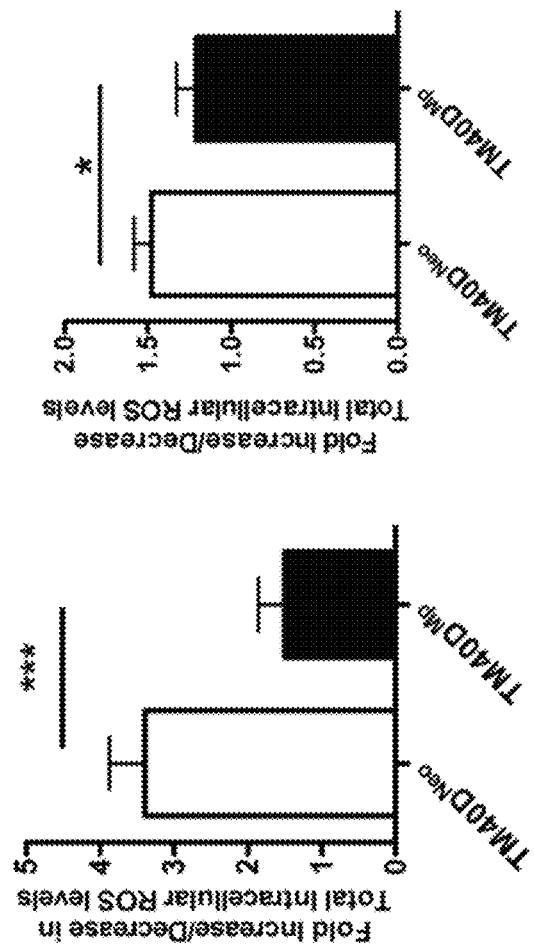
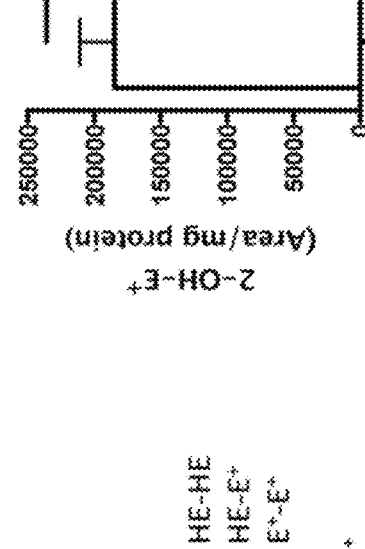
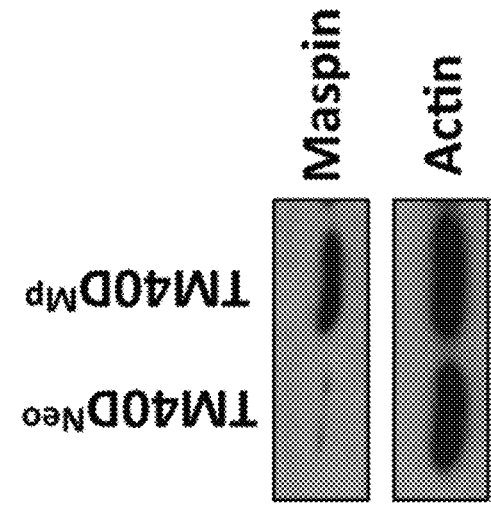
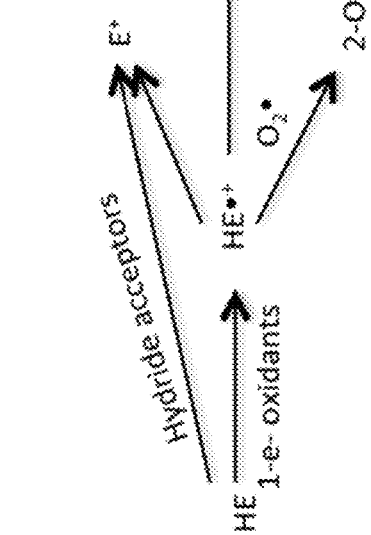
FIG. 2A  FIG. 2B  FIG. 2C  FIG. 2D  FIG. 2E

SEQUENCE LISTING

```
<160> NUMBER OF SEQ ID NOS: 13

<210> SEQ ID NO 1
<211> LENGTH: 13
<212> TYPE: PRT
<213> ORGANISM: Homo sapiens

<400> SEQUENCE: 1

Thr Asp Thr Lys Pro Val Gln Met Met Asn Met Glu Ala
1               5                   10

<210> SEQ ID NO 2
<211> LENGTH: 11
<212> TYPE: PRT
<213> ORGANISM: Homo sapiens

<400> SEQUENCE: 2

Ala Asn Ala Lys Val Lys Leu Ser Ile Pro Lys
1               5                   10

<210> SEQ ID NO 3
<211> LENGTH: 16
<212> TYPE: PRT
<213> ORGANISM: Homo sapiens
```

```
<400> SEQUENCE: 3

Asn Pro Ser Thr Met Ala Asn Ala Lys Val Lys Leu Ser Ile Pro Lys
1               5                   10                  15

<210> SEQ ID NO 4
<211> LENGTH: 23
<212> TYPE: PRT
<213> ORGANISM: Homo sapiens

<400> SEQUENCE: 4

Thr Asp Thr Lys Pro Val Gln Met Met Asn Met Glu Ala Thr Phe Cys
1               5                   10                  15

Met Gly Asn Ile Asp Ser Ile
            20

<210> SEQ ID NO 5
<211> LENGTH: 12
<212> TYPE: PRT
<213> ORGANISM: Homo sapiens

<400> SEQUENCE: 5

Ser Thr Ala Asn Ala Lys Val Lys Leu Ser Ile Pro
1               5                   10

<210> SEQ ID NO 6
<211> LENGTH: 12
<212> TYPE: PRT
<213> ORGANISM: Homo sapiens

<400> SEQUENCE: 6

Thr Ala Asn Ala Glu Val Lys Leu Ser Ile Pro Lys
1               5                   10

<210> SEQ ID NO 7
<211> LENGTH: 12
<212> TYPE: PRT
<213> ORGANISM: Homo sapiens

<400> SEQUENCE: 7

Ser Thr Glu Asn Ala Lys Val Lys Leu Ser Ile Pro
1               5                   10

<210> SEQ ID NO 8
<211> LENGTH: 15
<212> TYPE: PRT
<213> ORGANISM: Homo sapiens

<400> SEQUENCE: 8

Glu Asp Glu Ser Thr Gly Leu Glu Lys Ile Glu Lys Gln Leu Asn
1               5                   10                  15

<210> SEQ ID NO 9
<211> LENGTH: 27
<212> TYPE: PRT
<213> ORGANISM: Artificial sequence
<220> FEATURE:
<223> OTHER INFORMATION: maspin cysteine residues for Trx1 interaction
<220> FEATURE:
<221> NAME/KEY: MISC_FEATURE
<222> LOCATION: (16)..(19)
<223> OTHER INFORMATION: Xaa = any amino acid

<400> SEQUENCE: 9

Ala Leu Val Asp Leu Phe Lys Gln Leu Cys Glu Lys Glu Pro Gly Xaa
1               5                   10                  15
```

```
Xaa Xaa Xaa Ser Cys Phe Lys Gly Phe Phe Ile
            20                  25

<210> SEQ ID NO 10
<211> LENGTH: 21
<212> TYPE: PRT
<213> ORGANISM: Artificial sequence
<220> FEATURE:
<223> OTHER INFORMATION: maspin cysteine residues for Trx1 interaction

<400> SEQUENCE: 10

Ala Leu Val Asp Leu Phe Lys Gln Leu Cys Glu Pro Gly Ala Cys Phe
1               5                   10                  15

Lys Gly Phe Phe Ile
            20

<210> SEQ ID NO 11
<211> LENGTH: 27
<212> TYPE: PRT
<213> ORGANISM: Artificial sequence
<220> FEATURE:
<223> OTHER INFORMATION: maspin cysteine residues for Trx1 interaction
<220> FEATURE:
<221> NAME/KEY: MISC_FEATURE
<222> LOCATION: (16)..(19)
<223> OTHER INFORMATION: Xaa = any amino acid

<400> SEQUENCE: 11

Ala Leu Val Asp Leu Phe Lys Gln Leu Cys Glu Lys Glu Pro Gly Xaa
1               5                   10                  15

Xaa Xaa Xaa Ala Cys Leu Glu Asn Leu Gly Leu
            20                  25

<210> SEQ ID NO 12
<211> LENGTH: 21
<212> TYPE: PRT
<213> ORGANISM: Artificial sequence
<220> FEATURE:
<223> OTHER INFORMATION: maspin cysteine residues for Trx1 interaction

<400> SEQUENCE: 12

Ala Leu Val Asp Leu Phe Lys Gln Leu Cys Glu Pro Gly Ala Cys Leu
1               5                   10                  15

Glu Asn Leu Gly Leu
            20

<210> SEQ ID NO 13
<211> LENGTH: 375
<212> TYPE: PRT
<213> ORGANISM: Homo sapiens

<400> SEQUENCE: 13

Met Asp Ala Leu Gln Leu Ala Asn Ser Ala Phe Ala Val Asp Leu Phe
1               5                   10                  15

Lys Gln Leu Cys Glu Lys Glu Pro Leu Gly Asn Val Leu Phe Ser Pro
                20                  25                  30

Ile Cys Leu Ser Thr Ser Leu Ser Leu Ala Gln Val Gly Ala Lys Gly
            35                  40                  45

Asp Thr Ala Asn Glu Ile Gly Gln Val Leu His Phe Glu Asn Val Lys
        50                  55                  60

Asp Ile Pro Phe Gly Phe Gln Thr Val Thr Ser Asp Val Asn Lys Leu
65                  70                  75                  80
```

-continued

```
Ser Ser Phe Tyr Ser Leu Lys Leu Ile Lys Arg Leu Tyr Val Asp Lys
             85                  90                  95

Ser Leu Asn Leu Ser Thr Glu Phe Ile Ser Ser Thr Lys Arg Pro Tyr
            100                 105                 110

Ala Lys Glu Leu Glu Thr Val Asp Phe Lys Asp Lys Leu Glu Glu Thr
            115                 120                 125

Lys Gly Gln Ile Asn Asn Ser Ile Lys Asp Leu Thr Asp Gly His Phe
            130                 135                 140

Glu Asn Ile Leu Ala Asp Asn Ser Val Asn Asp Gln Thr Lys Ile Leu
145                 150                 155                 160

Val Val Asn Ala Ala Tyr Phe Val Gly Lys Trp Met Lys Lys Phe Pro
            165                 170                 175

Glu Ser Glu Thr Lys Glu Cys Pro Phe Arg Leu Asn Lys Thr Asp Thr
            180                 185                 190

Lys Pro Val Gln Met Met Asn Met Glu Ala Thr Phe Cys Met Gly Asn
            195                 200                 205

Ile Asp Ser Ile Asn Cys Lys Ile Ile Glu Leu Pro Phe Gln Asn Lys
            210                 215                 220

His Leu Ser Met Phe Ile Leu Leu Pro Lys Asp Val Glu Asp Glu Ser
225                 230                 235                 240

Thr Gly Leu Glu Lys Ile Glu Lys Gln Leu Asn Ser Glu Ser Leu Ser
            245                 250                 255

Gln Trp Thr Asn Pro Ser Thr Met Ala Asn Ala Lys Val Lys Leu Ser
            260                 265                 270

Ile Pro Lys Phe Lys Val Glu Lys Met Ile Asp Pro Lys Ala Cys Leu
            275                 280                 285

Glu Asn Leu Gly Leu Lys His Ile Phe Ser Glu Asp Thr Ser Asp Phe
290                 295                 300

Ser Gly Met Ser Glu Thr Lys Gly Val Ala Leu Ser Asn Val Ile His
305                 310                 315                 320

Lys Val Cys Leu Glu Ile Thr Glu Asp Gly Gly Asp Ser Ile Glu Val
            325                 330                 335

Pro Gly Ala Arg Ile Leu Gln His Lys Asp Glu Leu Asn Ala Asp His
            340                 345                 350

Pro Phe Ile Tyr Ile Ile Arg His Asn Lys Thr Arg Asn Ile Ile Phe
            355                 360                 365

Phe Gly Lys Phe Cys Ser Pro
            370                 375
```

MASPIN, MASPIN DERIVATIVES, AND MASPIN MIMETICS FOR REDUCING ROS, INFLAMMATION, AND SKIN AGING

CROSS-REFERENCE TO RELATED APPLICATIONS

The present application is a continuation of U.S. patent application Ser. No. 16/739,930, filed Jan. 10, 2020, now abandoned, which is a continuation of U.S. patent application Ser. No. 16/104,751, filed Aug. 17, 2018, now abandoned, which is a continuation of U.S. patent application Ser. No. 14/945,882, filed Nov. 19, 2015, now abandoned, which claims priority to U.S. Provisional Application Ser. No. 62/082,456, filed Nov. 20, 2014, each which is herein incorporated by reference in its entirety.

STATEMENT REGARDING FEDERAL FUNDING

This invention was made with government support under CA079736 awarded by the National Institutes of Health. The government has certain rights in the invention.

FIELD OF THE INVENTION

The present invention provides compositions, methods, and systems for treating inflammatory conditions (e.g., by inhibiting reactive oxygen species) in or on a subject with maspin, maspin derivatives, or maspin mimetics. In some embodiments, such agents are applied to the skin of a subject (e.g., to reduce skin aging).

BACKGROUND

Oxidative stress, a hallmark of many tumors, inflammatory response, and cell aging, is caused by an imbalance between the generation of reactive oxygen species (ROS) and cells' ability to clear oxidants. Processes associated with proliferation, apoptosis and senescence may be the result of activation of signaling pathways in response to intracellular changes in ROS. Thus, excessive production and inadequacy in a normal cell's antioxidant defense system can cause the cell to experience oxidative stress.

SUMMARY OF THE INVENTION

The present invention provides compositions, methods, and systems for treating inflammatory conditions (e.g., by inhibiting reactive oxygen species) in or on a subject with maspin, maspin derivatives, or maspin mimetics. In some embodiments, such agents are applied to the skin of a subject (e.g., to reduce skin aging) or internally to treat cancer.

In some embodiments, provided herein are methods of treating an inflammatory condition, or cancer, comprising: administering to a subject a composition comprising maspin, a maspin derivative, or a maspin mimetic. In certain embodiments, the administering is to the skin of a subject.

In certain embodiments, provided herein are compositions comprising: i) a human skin moisturizing lotion, and ii) maspin, a maspin derivative, or a maspin mimetic.

In some embodiments, provided herein are methods of treating an inflammatory condition and/or skin aging comprising: administering to a subject (e.g., who has symptoms of an inflammatory condition and/or skin aging) a composition (e.g., a pharmaceutical composition) comprising maspin, a maspin derivative, or a maspin mimetic.

In certain embodiments, the administering is to the skin of the subject (e.g., by applying a spray, lotion, cream, gel, ointment, or applying a skin patch). In particular embodiments, the composition further comprises skin lotion, cream, gel, or an ointment, a spray, or is present in a skin patch. In some embodiments, the skin of the subject is aging skin (e.g., the subject is a human that is over 50 . . . or over 60 . . . or over 70 . . . or over 80 . . . or over 90). In other embodiments, the skin of the subject is wrinkled. In additional embodiments, the skin has been damaged due to exposure to ultraviolet light.

In certain embodiments, the present disclosure provides methods of treating skin, skin conditions, and/or aging skin. In some embodiments, the methods are directed to improving skin appearance. For example, a composition such as described herein can be applied to the skin of a subject on or near areas in which an improvement in skin appearance is desirable, such as the face, or portions thereof, near or around the eyes and/or mouth, or the arms, legs, back, stomach, etc. In some embodiments, the methods are directed to reducing or preventing the appearance of skin wrinkles. In some embodiments, the methods are directed to improving the appearance of skin that has been damaged due to exposure to ultraviolet light (e.g., sunburned skin). In further embodiments, the methods are directed to improving the appearance of aging skin (e.g., by reducing or preventing the appearance of wrinkles and/or improving the elasticity of the aging skin).

In particular embodiments, the maspin derivative comprises an amino acid sequence selected from SEQ ID NOs:1-4. In other embodiments, the maspin derivative comprises an amino acid sequence selected from SEQ ID NOs:5-7. In some embodiments, the maspin derivative comprises the amino acid sequence in SEQ ID NO:8. In additional embodiments, the maspin derivative further comprises a peptide amphiphile. In further embodiments, the maspin derivative comprises (or consists of, or consists essentially of) an amino acid sequence selected from SEQ ID NOs:9-12. In additional embodiments, the maspin is full length, or at least 97%, 98%, or 99% of, full-length human maspin or its homologs in other species (e.g., rat, mouse, dog, etc.). In certain embodiments, the maspin is full-length human maspin minus 3-5 amino acids at the N, C or both termini.

In other embodiments, the subject has, or is suspected of having, symptoms of an inflammatory condition selected from the group consisting of: benign prostate hyperplasia (BPH), inflammatory bowel disease (IBD), ROS-induced obesity, diabetes, and atherosclerosis. In particular embodiments, the administering reduces or eliminates at least one of the symptoms of the inflammatory condition.

In some embodiments, provided herein are compositions comprising: i) a human skin moisturizing lotion, cream, gel, ointment, and ii) maspin, a maspin derivative, or a maspin mimetic. In other embodiments, provided herein is a skin patch device, wherein the skin patch comprises maspin, a maspin derivative, or a maspin mimetic (e.g., configured to be delivered over time to the skin of a subject wearing the patch).

In certain embodiments, provided herein are systems and kits comprising: i) a human skin moisturizing lotion, and ii) maspin, a maspin derivative, or a maspin mimetic. In some embodiments, the maspin derivative comprise an amino acid sequence selected from SEQ ID NOs:1-13.

DESCRIPTION OF THE FIGURES

FIGS. 1A-E. Total intracellular ROS levels in primary mammary epithelial cells isolated from WT and heterozygous maspin KO mice and maspin silenced immortalized human mammary epithelial MCF-10A. Total intracellular ROS levels were measured by flow cytometric analysis using Carboxy-DCFH-DA as a fluorogenic substrate. (A) Western blot analysis of maspin expression in primary mammary epithelial cells isolated from WT and heterozygous maspin KO mice. Equal amount of proteins (25 µg/lane) were loaded and immunobloted for maspin and actin (a loading control). (B) Constitutive levels of ROS in primary mammary epithelial cells isolated from WT and heterozygous maspin KO mice (n=3). (C) ROS level in primary mammary epithelial cells isolated from WT and heterozygous maspin KO mice (n=3) after treatment with $H_2O_2$ (250 µM) for 3 hrs. (D) Western blot analysis of maspin expression in immortalized human mammary epithelial MCF-10A and MCF-10A229 cells. (E) ROS level in immortalized human mammary epithelial MCF-10A and MCF-10A229 (maspin silenced) cells after treatment with $H_2O_2$ (250 µM) for 3 hrs. Data shown are mean+SD of three independent experiments. Asterisks indicate significance according to t-test (two-tailed); *$p<0.05$, $p<0.01$, *$p<0.001$ FIGS. 2A-E. Maspin overexpressing tumor cells are resistant to oxidative stress. (A) Western blot analysis of maspin expression in TM40DNeo and TM40DMp cells. Equal amount of proteins (25 µg/lane) were loaded and immunobloted for maspin and actin (a loading control). (B) ROS level in TM40DNeo and TM40DMp cells after treating with $H_2O_2$ (250 µM) for 3 hrs. (C) ROS level in TM40DNeo and TM40DMp cells after treating with antimycin-A (100 µM) for 1 hr. (D) Schematic representation of oxidation of hydroethidine (HE) and formation of various oxidation products. 2-hydroxyethidium (2-OH-E+) is the primary product of the reaction of HE and superoxide (O2°-) and other products like E+ and dimers of HE (HE-HE, HE-E+, E+-E+) are indicators of one electron oxidants. (E) Levels of superoxide (2-OH-E+) in TM40DNeo and TM40DMp cells after treating with STS (1 µM) for 3 hrs as measured by HPLC-MS. The results are shown as area under peak per mg of protein. Data shown are mean+SD of three independent experiments. Asterisks indicate significance according to t-test (two-tailed); *$p<0.05$, ***$p<0.001$.

DETAILED DESCRIPTION

The present invention provides compositions, methods, and systems for treating inflammatory conditions (e.g., by inhibiting reactive oxygen species) in or on a subject with maspin, maspin derivatives, or maspin mimetics. In some embodiments, such agents are applied to the skin of a subject (e.g., to reduce skin aging).

Maspin, a member of the serine protease inhibitor (serpin) superfamily, displays tumor suppressing activity by controlling cell migration, proliferation, apoptosis and adhesion. Provided herein is evidence that maspin acts as a reactive oxygen species (ROS) scavenger through oxidation of three structurally exposed cysteine thiols to sulfenic acid. Ablation of these cysteine residues in maspin results in a significant increase in total ROS production in TM40D mouse mammary cells. Also, the cells containing triple cysteine mutant of maspin show elevated ERK1/2 activity, a downstream target of ROS, and enhanced proliferation and colony formation. These findings establish a novel mechanism by which maspin utilizes its cysteine thiols to inhibit oxidative stress and cell growth. In addition, Maspin's anti-ROS property may be used against inflammation-induced responses and skin aging. Inflammation can be induced due to excessive free radicals and oxidative stress. Inhibiting ROS using maspin may block inflammatory response. Skin aging is well known to be regulated by an imbalance in cellular ROS of skin epithelial cells. Topical application of recombinant maspin may inhibit ROS level and block skin aging process.

Maspin is endogenously expressed in epithelial cells and its expression can be up-regulated by a range of factors. Maspin mimetic peptides can be designed to mimick whole protein effect against ROS, making it easier to produce for treatment. Recombinant maspin or its derivative including mimetic peptides may be applied topically on skin to inhibit cellular ROS, while excessive skin cell ROS is critical for skin cell aging. Thus, maspin and its derivative may be used as an anti-aging product for skin care.

Maspin has eight cysteine residues, which prompted an exploration of cysteine-targeted oxidation of this multifaceted protein in the regulation of ROS metabolism. It was found that only three cysteine residues, located at positions C183, C205, and C323 are structurally fully exposed. Given the anti-oxidant capacity of the cysteine thiol group, it was hypothesized and proved that these exposed cysteine residues in maspin act as a potent scavenger/quencher of ROS. Maspin overexpressing cells are more resistant to oxidative stress and this property is attributed to the cysteine residues in maspin. Recombinant maspin serves to inhibit ROS in the cell-free system.

Figure 3A:
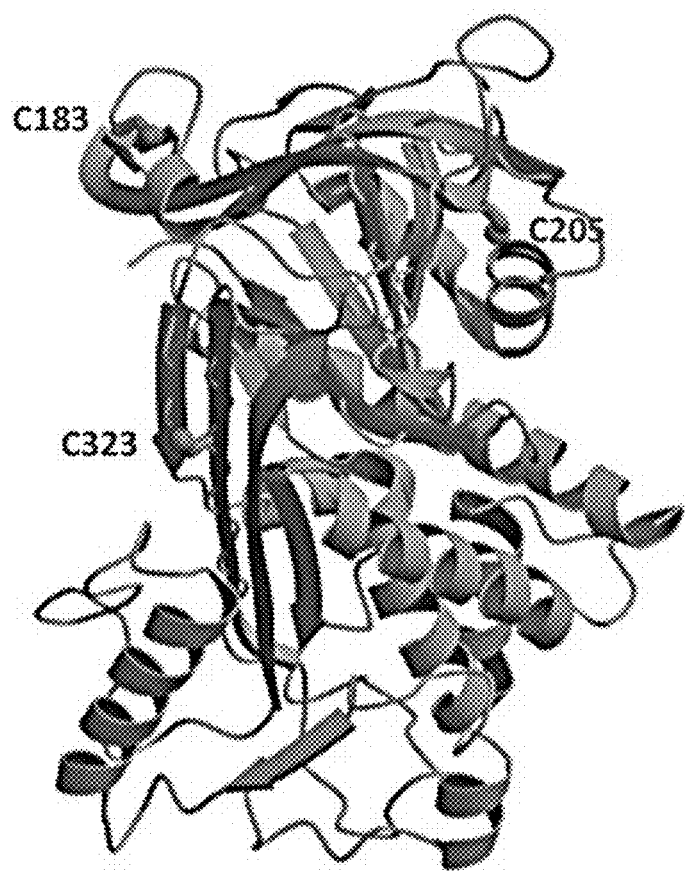
FIGS. 3A-D. Importance of cysteine residues and role in oxidative stress. (A) Three dimensional structure of maspin highlighting three cysteine residues were mutated to serine at position 183, 205 and 323. (B) Western blot analysis of maspin expression in TM40DNeo, TM40DMp, TM40DT and other maspin mutant cells. Equal amount of proteins (25 µg/lane) were loaded and immunobloted for maspin and actin (a loading control). (C) Comparison of total intracellular ROS levels in various TM40D cells treated with $H_2O_2$ (250 µM) for 3 hrs as determined by flow cytometric analysis. (D) Constitutive levels of GSH/GSSG ratio in TM40DNeo, TM40DMp and TM40DT cells. Data shown are mean+SD of three independent experiments. Asterisks indicate significance according to t-test (two-tailed); $p<0.01$, *$p<0.001$ compared with TM40DMp; #$p<0.05$ compared with TM40DT.

Maspin acts as a reactive oxygen species (ROS) scavenger. Three structurally exposed cysteine thiols in maspin are responsible for this anti-ROS function. These bases have been identified as C183, C205, and C323. Their relative position in three dimension structure is shown in FIG. 3A. In addition, other cysteine residues (C20, C287, and C373) in maspin are identified to play a role in ROS inhibition, by forming intramolecular disulfide bond and interacting with Trx1.

In certain embodiments, a maspin derivative is employed in the methods, kits, and compositions herein. Exemplary maspin derivative sequences are provided in Table 1 below. Such sequence, alone, or with additional maspin or non-maspin amino acids at either end (or other molecules such as peptide amphiphiles) may be employed.

Table 1

A. Maspin truncated peptides
 (SEQ ID NO: 1)
1. amino acids 190-202: TDTKPVQMMNMEA;

(SEQ ID NO: 2)
2. s2C 265-274: ANAKVKLSIPK;

(SEQ ID NO: 3)
3. NPSTMANAKVKLSIPK;

(SEQ ID NO: 4)
4. TDTKPVQMMNMEATFCMGNIDSI: 181-202 and 190-211;

B. Maspin derivative peptides
 (SEQ ID NO: 5)
5. STANAKVKLSIP;

(SEQ ID NO: 6)
6. TANAEVKLSIPK;

(Seq ID NO: 7)
7. STENAKVKLSIP;

-continued
C. Maspin G-helix peptide (effective component for the maspin nanopeptide MMPA)
 (SEQ ID NO: 8)
8. EDESTGLEKIEKQLN;

D. Additional maspin cysteine residues for Trx1 interaction
 (SEQ ID NO: 9)
9. ALVDLFKQLCEKEPG-XXXX-SCFKGFFI;

(SEQ ID NO: 10)
10. ALVDLFKQLCEPGACFKGFFI;

(SEQ ID NO: 11)
11. ALVDLFKQLCEKEPG-XXXX-ACLENLGL;

(SEQ ID NO: 12)
12. ALVDLFKQLCEPGACLENLGL.

In the above, "X" may be any amino acid residue. Also, the sequence, such as SEQ ID NO:8, may be part of a peptide-amphiphile as described, for example, in Pat. Pub. US20140256635, which is herein incorporated by reference in its entirety, particular for MMPA constructs. In certain embodiments, one or more additional human maspin amino acids (or other amino acids) are added to the ends of the sequences shown in Table 1 (e.g., 5-25 or 25-50 additional amino acids from human maspin are added). In certain embodiments, the maspin employed is full length or at least 99% of full-length human maspin. A full length human maspin is found at Genbank accession number AAA18957, which provides the full human protein. This full length protein is also shown below:

(SEQ ID NO: 13)
  1  mdalqlansa favdlfkqlc ekeplgnvlf spiclstsls laqvgakgdt aneigqvlhf 61  envkdipfgf qtvtsdvnkl ssfyslklik rlyvdkslnl stefisstkr pyakeletvd 121  fkdkleetkg qinnsikdlt dghfenilad nsvndqtkil vvnaayfvgk wmkkfpeset 181  kecpfrlnkt dtkpvqmmnm eatfcmgnid sinckiielp fqnkhlsmfi llpkdvedes 241  tglekiekql nseslsqwtn pstmanakvk lsipkfkvek midpkaclen lglkhifsed 301  tsdfsgmset kgvalsnvih kvcleitedg gdsievpgar ilqhkdelna dhpfiyiirh 361  nktrniiffg kfcsp.

Maspin and maspin derives from other, non-human species may also be employed. For example, maspin from mouse (AAB06042), rat (AAB06043), horse, cow, dog, cat, etc.

In certain embodiments, the compositions (comprising the maspin, maspin derivatives or mimetics) are formulated in a format selected from the group consisting of a cream, a lotion, a spray, an ointment, a gel, a powdered mask, a paste, a cleanser, and a foundation. In other embodiments, such compositions are present in a patch. In particular embodiments, the compositions may include one or more additives selected from the group consisting of: a perfume, colorant, thickening agent, vegetable oil, emulsifier, solvent, pH adjusting agent, antiseptic agent, preservative, vitamin, sunblock, surfactants and combinations thereof. Various physical sunscreen agents such as titanium dioxide, silicone-treated titanium dioxide, zinc oxide, ferrous oxide, ferric chloride, talc, chromium oxide, or cobalt oxides may be included. Alternatively or in addition, a chemical sunscreen agent such as para-amino benzoic acid, esters of para-amino benzoic acid, salicylates, cinnamates, benzophenones, dihydroxyacetone, PARSOL 1789, or melanin may be included.

In certain embodiments, the compositions disclosed herein are used to treat a subject who has, or is suspected of having, symptoms of an inflammatory condition, such as, but not limited to: benign prostate hyperplasia (BPH), inflammatory bowel disease (IBD), ROS-induced obesity, diabetes, and atherosclerosis. In particular embodiments, administering the composition to the subject (e.g., intravenously) reduces or eliminates at least one of the symptoms of the inflammatory condition.

Compositions for such in vivo administration to a subject can be formulated in pharmaceutical compositions. Such pharmaceutical composition, besides containing maspin, maspin derivatives or mimetics, may contain additional agents. It is not intended that the present invention be limited by the particular nature of the pharmaceutical preparation. For example, such compositions can be provided together with physiologically tolerable liquid, gel or solid carriers, diluents, adjuvants and excipients. These therapeutic preparations can be administered to mammals for veterinary use, such as with domestic animals, and clinical use in humans in a manner similar to other therapeutic agents. In general, the dosage required for therapeutic efficacy will vary according to the type of use and mode of administration, as well as the particularized requirements of individual hosts.

Such compositions are typically prepared as liquid solutions or suspensions, or in solid forms. Oral formulations usually will include such normally employed additives such as binders, fillers, carriers, preservatives, stabilizing agents, emulsifiers, buffers and excipients as, for example, pharmaceutical grades of mannitol, lactose, starch, magnesium stearate, sodium saccharin, cellulose, magnesium carbonate, and the like. These compositions take the form of solutions, suspensions, tablets, pills, capsules, sustained release formulations, or powders, and typically contain 1%-95% of active ingredient, preferably 2%-70%. The compositions are also prepared as injectables, either as liquid solutions or suspensions; solid forms suitable for solution in, or suspension in, liquid prior to injection may also be prepared. The compositions of the present invention may be mixed with diluents or excipients which are physiological tolerable and compatible. Suitable diluents and excipients are, for example, water, saline, dextrose, glycerol, or the like, and combinations thereof. In addition, if desired the compositions may contain minor amounts of auxiliary substances such as wetting or emulsifying agents, stabilizing or pH buffering agents.

Additional formulations which are suitable for other modes of administration, such as topical administration, include salves, tinctures, creams, lotions, and, in some cases, suppositories. For salves and creams, traditional binders, carriers and excipients may include, for example, polyalkylene glycols or triglycerides.

In some embodiments, the pharmaceutical composition are administered to a subject, or applied to the skin of a subject, in an amount within the range of from about 0.01 mg/kg to about 100 mg/kg (maspin or maspin derivative per kg of patient), although higher and lower doses may be utilized. For example, in some embodiments, between about 100-200, 200-400, 400-800, or 800-1000 mg/kg or more of maspin or maspin derivative is administered or applied.

Anti-ROS reagents have exciting potential in cancer therapy as a strategy to control tumor growth. Because maspin is expressed endogenously in the epithelial cells, it is possible one can upregulate maspin to enhance cell's ability against ROS thereby inhibiting cancer initiation. This property may be used as a novel cancer therapy. Both inflammatory response and aging are influenced by ROS. Inhibiting ROS can block inflammatory responses and aging. Maspin's anti-ROS property may be us used as a topically applied reagent against skin aging or other inflammatory diseases. The following are inhibitors against oxidative stress currently under development: BG 12—Biogen Phase III drug-anti—Ros agent; and NAC—Medicinal Nutraceutics-N-Acetyl Cysteine (NAC)—Capsules currently in the market.

EXAMPLES

Example 1

Use of Maspin as an Anti-ROS Scavenger Against Cell Proliferation, Inflammation, and Aging Experimental Procedures Plasmid constructs and cell culture—Maspin X-ray crystal structure was reported by Law et al. (16) and Al-Ayyoubi et al. (17). Molsoft ICM-pro Version 3.48 was used to analyze the X-ray structure of human maspin (PDB ID: 1xu8), as reported by Law et al (16) to analyze the presence of exposed cysteine residues, which can serve as site for oxidation. QuikChange II site-directed mutagenesis kit (Stratagene) was used to mutate cysteine residues to serine residues in pEF-IRES-neo-h.maspin using the specific mutagenic primers (Table-S1). Mutations in the plasmid were confirmed by DNA sequencing.

Murine mammary tumor TM40D cells were used and maintained as described previously (18). TM40D cells were transfected with pEF-IRES-neo-h.maspin wild type (Mp), triple mutation (T) or control vector alone (Neo) by Effectent reagent (Qiagen). The stable transfectants were selected with G418 medium (600 μg/ml) for 14 days and expression of maspin was confirmed by Western blot analysis. The GST fusion proteins [GST-h.maspin (GST-MpWT) and GST-h.maspin triple mutation (GST-MpT)] were induced by IPTG (1 mM), and purified using glutathione agarose (Sigma). Thrombin was used to cleave the maspin from the agarose beads. The size and purity of proteins were confirmed by SDS-PAGE and Western blot analysis.

Human mammary tumor and immortalized epithelial cells (MCF-7, MCF-10A, MCF-10A229) were maintained as described previously (19). In a previous study, it was shown that maspin homozygous knockout mice (KO) are embryonically lethal (20), therefore, mouse primary mammary epithelial cells from wildtype (WT) were isolated and maspin heterozygous knockout mice as described earlier (21). Western Blot Analysis—Cell Lysates were Prepared in RIPA Buffer with Protease Cocktail Inhibitor (Thermo Scientific).

Cellular debris was cleared from lysates by centrifugation and protein concentration was determined by the BCA Protein Assay (Pierce). Samples were separated on 10% SDS-PAGE, transferred to a PVDF membrane (GE Healthcare) and blotted with rabbit anti-maspin AbS4A antibody (3) and anti-actin antibody (Cat No. A2066. Sigma). HRP labeled goat anti-rabbit polyclonal antibody was used as a secondary antibody and proteins were visualized with enhanced chemiluminescence substrate (Pierce).

Quantification of Reactive Oxygen Species (ROS)—Flurogenic substrate carboxy-2', 7'-dicholorodi hydrofluorescein diacetate (DCFH-DA) was used to detect intracellular ROS (22). Briefly, $10^6$ cells in 6-well plate were plated and incubated at 37° C. overnight. Next day, the culture medium was discarded and cells were washed twice with PBS followed by incubation with 20 μM Carboxy-DCFH-DA at 37° C. for 30 minutes in serum free medium. Cells that were either untreated or treated with different ROS inducers at the indicated final concentrations were incubated at 37° C. for indicated time periods. At the end of the exposure period, cell supernatants were discarded; cells were washed with PBS and harvested using Trypsin/EDTA. Cells were transferred to FACS tubes and 20,000 events were analyzed using a BC Epics XL Analyzer with an excitation wavelength of 488 nm and an emission wavelength of 525 nm. Results were depicted as fold change in fluorescent intensity.

Measurement of Superoxide ($O2°-$) levels—To measure superoxide levels in the cell culture, we used 2,7-Diamino-10-ethyl-9-phenyl-9,10-dihydrophenanthridine, 3,8-Diamino-5,6-dihydro-5-ethyl-6-phenylphenanthridine hydroethidine (HE) a fluorogenic probe, which is widely used to detect superoxide levels (23). TM40DNeo and TM40DMp cells were treated with staurosporine (STS; 1 μM) for 3 hrs and incubated with 10 μM HE for 1 hr. Treating cultured cells with STS is known to induce a rapid and prolonged increase in ROS (24,25). Cells were washed twice with cold PBS, scraped and kept for 30 minutes on ice. Cell suspension was centrifuged at 1000×g for 5 minutes at 4° C. Pellets were either stored at −80° C. or immediately processed for HPLC analysis. Cells were lysed using 0.1% Triton X-100 in DPBS. Cell lysates were mixed with an equal amount of 0.2 M solution of HClO4 in MeOH, and left undisturbed for 2 hrs to allow protein precipitation. Samples were centrifuged for 30 minutes at 20,000 g at 4° C. and 100 μl of supernatant was mixed with an equal amount of 1 M solution of potassium phosphate buffer (pH 2.6). After, centrifuging at 20,000 g for 15 minutes at 4° C., sample were analyzed by HPLC-MS. Instrumental setup for the analysis of HE and its oxidation products by HPLC-MS is depicted in Table-S2. HPLC peak areas were normalized to protein concentration.

Cell-extracellular matrix (ECM) adhesion assay—Adhesion of mouse mammary TM40DNeo cells to extracellular matrix matrigel (BD Biosciences) was used to determine the biological activity of recombinant proteins. Adhesion assay was performed as described by Corbett et al (26). Briefly, cells were suspended in medium containing 100 nM of maspin (GST.MpWT and GST.MpT) or GST, and then cultured on matrigel coated 96-well plate at a density of 5×104 cells/well in triplicates for 4 hrs. The plates were washed twice with PBS and incubated with 50 μl of hexosaminidase substrate (3.75 mM 4-Nitrophenyl N-acetyl-β-D-glucosaminide, 0.25% Triton X-100, 0.05 M citrate buffer, pH 5) for 1.5 hrs at 370 C. After incubation 75 μl of development buffer (5 mM EDTA, 50 mM glycine, pH 10.4) was added and the readings were recorded at 405 nm.

Measurement of GSH/GSSG ratios— A luminescence-based system was used for detection and quantification of GSH/GSSG ratios in cultured cells (Cat No. V6611, Promega).

Detection of protein sulfenic acid modifications—Detection of protein sulfenic acid in vitro was done as described previously (14,15,27). Briefly, equal amounts (62.5 ng) of thrombin cleaved WT (MpWT) and triple mutated (MpT) recombinant maspin proteins were oxidized with $H_2O_2$ (1 mM) for 1 minute in the presence of dimedone (10 mM). The oxidation of cysteine residues was detected by Western blot analysis using an antibody (Millipore; Cat No. 07-2139) that specifically recognizes dimedone derivatized cysteine sulfenic acid residues.

Trapping of sulfenic acid in cells (Immunoprecipitation)—Cells were first treated with $H_2O_2$ (250 μM) for 3 hrs and then lysed in lysis buffer: 100 mM Tris (pH 7.4), 1% Triton X-100, protease inhibitor mixture (Thermo Scientific) with or without dimedone (10 mM) for 45 minutes before the addition of N-ethylmaleimide to a final concentration of 100 mM for another 10 minutes. Cellular debris was cleared from lysates by centrifugation, and protein concentration was determined by the BCA Protein Assay (Pierce). Whole cell extracts (1 mg) were incubated overnight (constant rocking) with 0.5 μg of rabbit anti-maspin AbS4A antibody (3) or control rabbit IgG at 4° C. Protein A-Sepharose-coupled beads (Amersham Biosciences) were added and incubated for 1 hr at 4° C. under constant agitation. Beads were centrifuged, washed briefly with ice-cold lysis buffer, and finally incubated with elution buffer for 15 minutes at room temperature. Samples were mixed with non-reducing buffer (5×) and separated on SDS-PAGE gels, transferred to a PVDF membrane (GE Healthcare), and probed for maspin, cysteine sulfenic acid and IgG. Appropriate secondary antibodies were added, and proteins were visualized with enhanced chemiluminescence substrate (Pierce). Anti-Cysteine Sulfenic Acid was obtained from Millipore (Cat No. 07-2139), which recognizes proteins containing the dimedone-bound cysteine sulfenic acid.

Soft agar colony formation assay—As described previously (28), 6-well dishes were plated with bottom agar (0.7% agarose) for 30 minutes. Cells were mixed with the top agar (0.3% agarose) at a concentration of $5×10^4$ cells per well and allowed to solidify. The cells were fed every 5th day with media and grown at 37° C. for 3 weeks, cells stained for 1 hr with 0.05% crystal violet and the numbers of purple colored colonies were counted as 10 fields per well at 40× using Image J software with a cut off range of 20-5000 pixels.

MTT in vitro cell proliferation assay—Cells were seeded at $10^3$ cells/well in 96—well plate and allowed to grow at 37° C. with 5% $CO_2$. At each time point MTT (3-(4, 5-dimethylthiazolyl-2)-2, 5 diphenyltetrazolium bromide) reagent (5 mg/ml) was added in a volume of 10 μl per well and incubated at 37° C. with 5% $CO_2$ for 3 hrs. The media was aspirated and 100 μl of DMSO was added and mixed until a uniform purple color was formed. The cell samples were measured using a plate reader at 570 nm. Assays were performed in triplicates.

ERK1/2 phosphorylation—Protein lysates (30 μg) were separated on 12% SDS-PAGE and phospho-plus kit was used to determine the ERK1/2 phosphorylation (Cat No. 9100, Cell Signaling Technology).

Statistical Analysis—All the experiments were carried out three times or as stated. Quantification of Western Blots was performed using Scion Image. Statistical analysis (two tailed t-test) was based on a minimum of three replicates using Prism statistical software. The differences were considered significant if $p<0.05$.

Results

Status of intracellular ROS levels in primary mouse mammary epithelial cells isolated from wildtype (WT) and heterozygous maspin knockout (KO) mice and maspin silenced immortalized human mammary epithelial MCF-10A cells. In order to understand the role of maspin in oxidative stress, we isolated primary mammary epithelial cells from WT and maspin heterozygous KO mice and measured their ROS levels. FIG. 1A depicts the Western blot analysis for maspin expression in cells isolated from WT and maspin heterozygous KO mice. We observed that the cells isolated from maspin KO mice had significantly higher intracellular ROS levels as compared with WT mice (p<0.001; FIG. 1B). We also observed a significant increase in ROS production in KO cells as compared with WT cells when they were pre-treated with $H_2O_2$ for 3 hrs (p<0.05; FIG. 1C). To further analyze the importance of maspin in ROS production, we used maspin-silenced MCF-10A cells (MCF-10A229), which as confirmed by Western blot analysis, showed attenuated levels of maspin (FIG. 1D). MCF-10A cells displayed significantly lower levels of ROS as compared with the maspin-silenced cells MCF-10A229 cells (p<0.01; FIG. 1E). Collectively, these results indicate that presence of maspin in primary and in immortalized mammary epithelial cells make them more efficient to quench ROS and therefore, indicate the importance of maspin in ROS regulation.

Maspin overexpressing cells are resistant to oxidative stress—To directly target the importance of maspin in oxidative stress, TM40D mouse mammary epithelial cell line that expresses low levels of maspin, was used as a cellular model (FIG. 2A). Maspin was over expressed in TM40D cells (FIG. 2A) and total intracellular ROS levels were measured. Our results demonstrated that the exposure for 3 hrs to 250 μM $H_2O_2$ was sufficient to induce significant increase in intracellular ROS in TM40DNeo cells as compared to maspin overexpressing TM40DMp cells (p<0.001; FIG. 2B).

To determine the physiological relevance or the effect of endogenous ROS on mammary epithelial cells, we used antimycin-A, a compound that inhibits electron transport at complex III of the mitochondrial respiratory chain, thereby, inducing the production of superoxide and other ROS in the cells (29,30). Treating cells with antimycin-A resulted in decreased ROS levels in maspin overexpressing cells (p<0.05; FIG. 2C).

Additionally, hydroethidine (HE) was used to determine the superoxide ($O2°-$) levels as an indicator of oxidative stress in response to an alternative ROS inducer i.e. staurosporine (STS) using HPLC-MS in TM40DNeo and TM40DMpcells. FIG. 2D depicts the schematic representation of the reaction of HE and superoxide radical anion ($O2°-$) to form 2-hydroxyethidine (2-OH-E+). We observed a significant decrease in the levels of superoxide in maspin overexpressing cells as compared to TM40DNeo cells in response STS treatment (p<0.05; FIG. 2E).

Cysteine residues in maspin control oxidative stress—Having established that maspin is involved in modulating oxidative stress in normal mammary epithelial and cancer cells, we further sought to identify the underlying mechanism of maspin action. Due to presence of active thiol [—SH] group, cysteine residues play an important role as oxidative stress sensors in various proteins (12,13). Using Molsoft ICM-pro Version 3.48, we analyzed the X-ray structure of human maspin protein reported by Law et al. (PDB ID: 1xu8) (16). We identified that out of eight cysteine residues present in human maspin only three residues at the position 183, 205, and 323 were structurally exposed, which might serve as possible sites for oxidation. In contrast, cysteine residues at position 20, 34, 214, 287, 373 were found to be buried. Previously, it has been shown that mutating all the cysteines to serine/alanine by site directed mutagenesis does not change the structure of maspin (17).

Figure 3B:
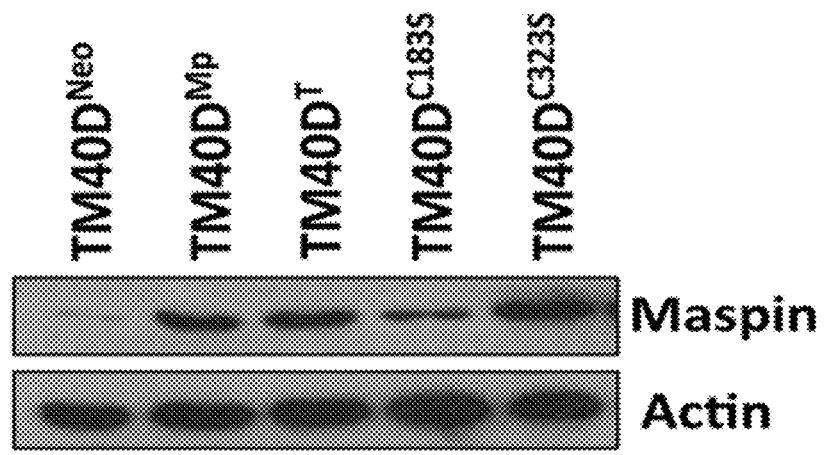

Therefore, we mutated either single (C183 or C323) or all the three exposed cysteine residues to serine. FIG. 3A depicts three-dimensional structure of maspin demonstrating three structurally exposed (C183, C205 and C323) cysteine residues. TM40D cells were transfected with different maspin cysteine mutants and expression of maspin was confirmed by Western blot analysis (FIG. 3B).

Figure 3C:
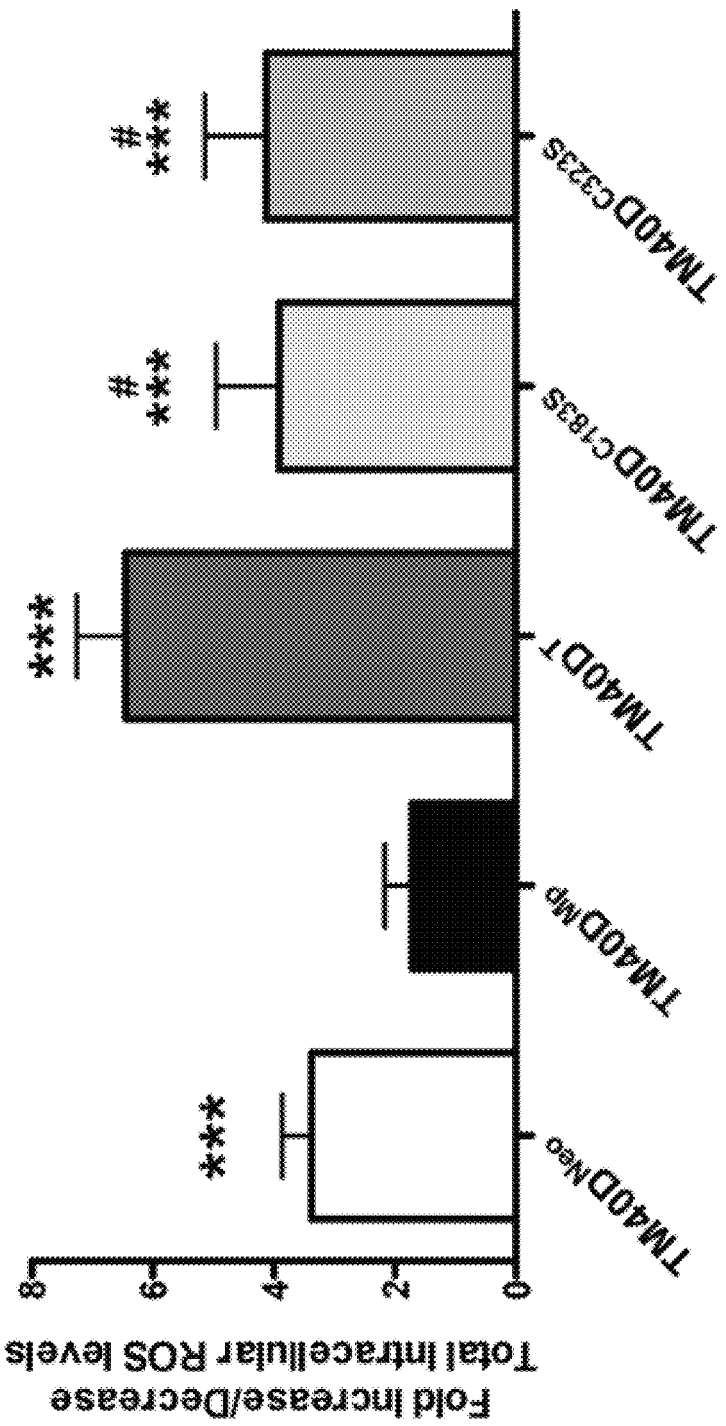

Mutating a single cysteine residue i.e. 183 or 323 individually in maspin led to a two-fold increase in ROS levels in comparison to TM40DMp cells (FIG. 3C); suggesting that both these cysteine residues are equally important in regulating cellular ROS. When all the three surface cysteines were mutated, cellular ROS level in TM40DT was further increased (~1.4 fold) compared with TM40DC183S or TM40DC323S cells (p<0.05; FIG. 3C). Increased ROS levels in TM40DT correlated with the absence of surface-exposed cysteine residues, thereby establishing the importance of maspin cysteine residues in modulating ROS.

Figure 3D:
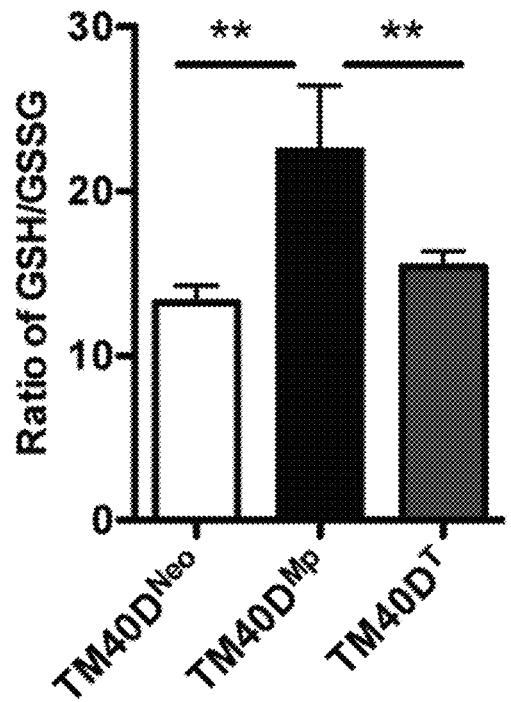

Enzymes such as those involved in glutathione redox cycle play an important role in detoxification of various oxidant species (31). A decreased GSH/GSSG ratio is considered indicative of increased oxidative stress (32,33). We found that overexpression of maspin in TM40D cells resulted in an increased ratio of GSH/GSSG (p<0.01; FIG. 3D). However, expressing triple mutant maspin in TM40D cells resulted in a decreased ratio of GSH/GSSG as compared with cells expressing WT maspin in the absence of ROS stimulus (p<0.01; FIG. 3D).

Figure 4A:
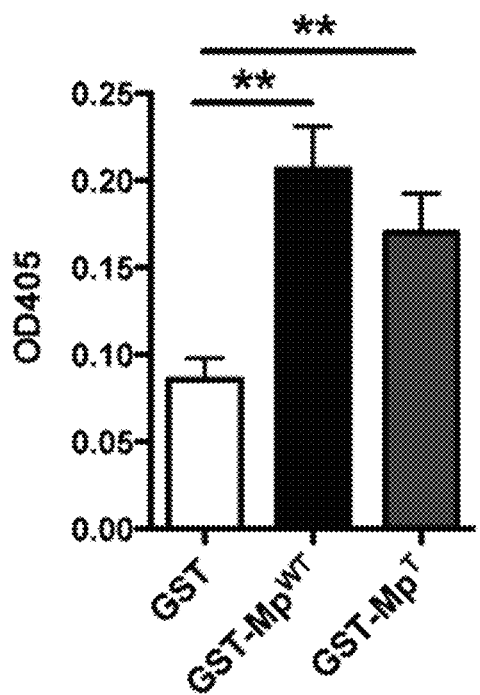
FIGS. 4A-D. Triple mutated maspin is biologically active and evidence for oxidation of cysteine to sulfenic acid. (A) Mutated maspin retains the ability to enhance cell adhesion to extracellular matrix (ECM). Increased adhesion of TM40DNeo cells to matrigel ECM was observed when cells were pretreated with wild type and triple mutated recombinant maspin (100 nM) as compared to its GST control. (B) Biochemistry of oxidation of thiol group [—SH] and capturing of sulfenic acid [—SOH] using dimedone. Protein thiols [—SH], which are susceptible to oxidation by ROS, generate sulfenic acid [—SOH] and largely irreversible sulfinic acid [—$SO_2H$] and sulfonic acid [—$SO_3H$]. Sulfenic acid can be labeled by dimedone or dimedone based chemicals. (C) Equal amounts (62.5 ng) of WT and Triple mutated maspin were oxidized with $H_2O_2$ (10 mM) for 1 minute in presence of dimedone (10 mM) and oxidation of cysteine residues was detected by Western blot analysis using antibody, which specifically recognize dimedone derivatized cysteine sulfenic acid residues (D) Cells were treated with $H_2O_2$ (250 µM) for 3 hrs and then lysed in presence or absence of Dimedone (10 mM). Maspin was immunoprecipitated and then immunobloted with maspin antibody and antibody, which specifically recognizes dimedone derivatized cysteine sulfenic acid residues. Data shown are mean+SD of three independent experiments. Asterisks indicate significance according to t-test (two-tailed); $p<0.01$, *$p<0.001$.
Figure 4B:
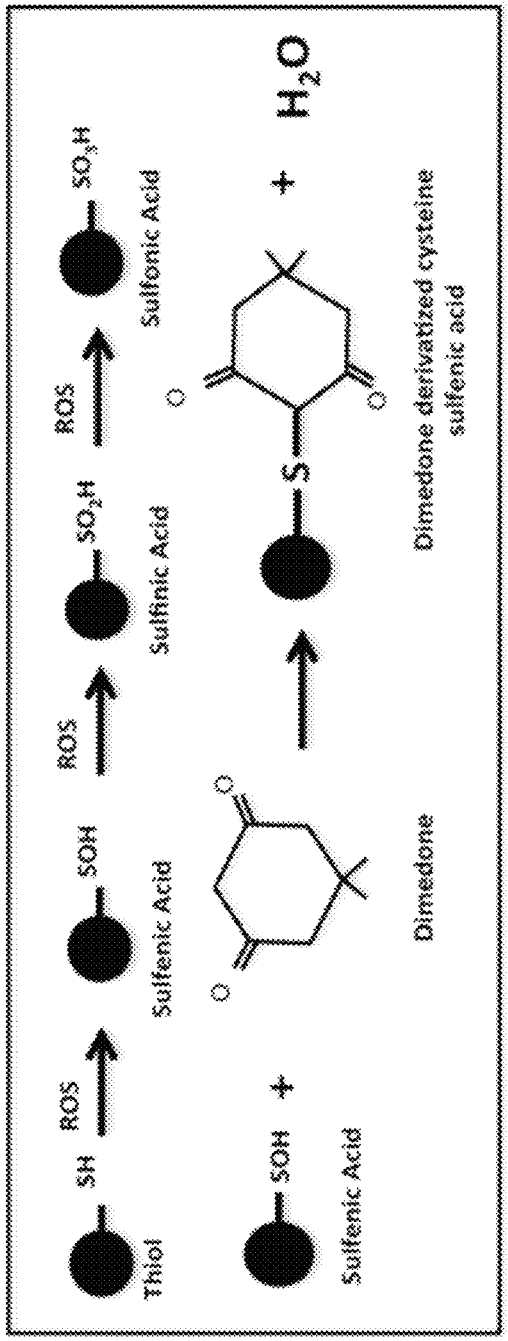
Figure 4C:
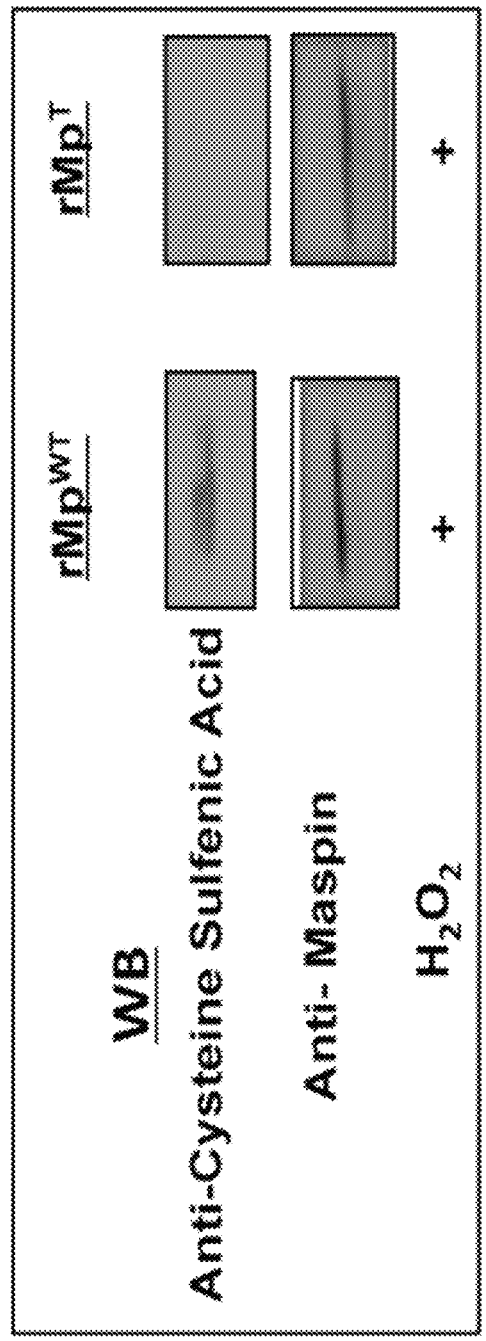

Triple mutated maspin is biologically active and evidence for oxidation of cysteine thiol to sulfenic acid—To confirm that mutated maspin retains its normal biological activity we tested whether the triple mutated recombinant maspin (GST.MpT) could increase cell adhesion to ECM matrix as similar to WT maspin protein (GST.MpWT). Increased adhesion of TM40DNeo cells to matrigel matrix was observed when cells were pretreated with GST.MpT compared to its control (p<0.01; FIG. 4A). In order to elucidate whether selected cysteine residues of maspin traps free radicals or other oxidants, WT and triple mutated recombinant maspin proteins were treated with hydrogen peroxide in presence or absence of dimedone. Dimedone is a highly specific agent that reacts with cysteine sulfenic acid (14,15). Sulfenic acid is the initial oxidation product which subsequently reacts with dimedone to form a stable covalent bond (15) (FIG. 4B). When probed with anti-cysteine sulfenic acid antibody, we observed an absence of signal in lanes loaded with triple mutated maspin as compared to WT maspin (FIG. 4C). These results clearly demonstrate oxidation of thiol groups to cysteine sulfenic acid in maspin.

Figure 4D:
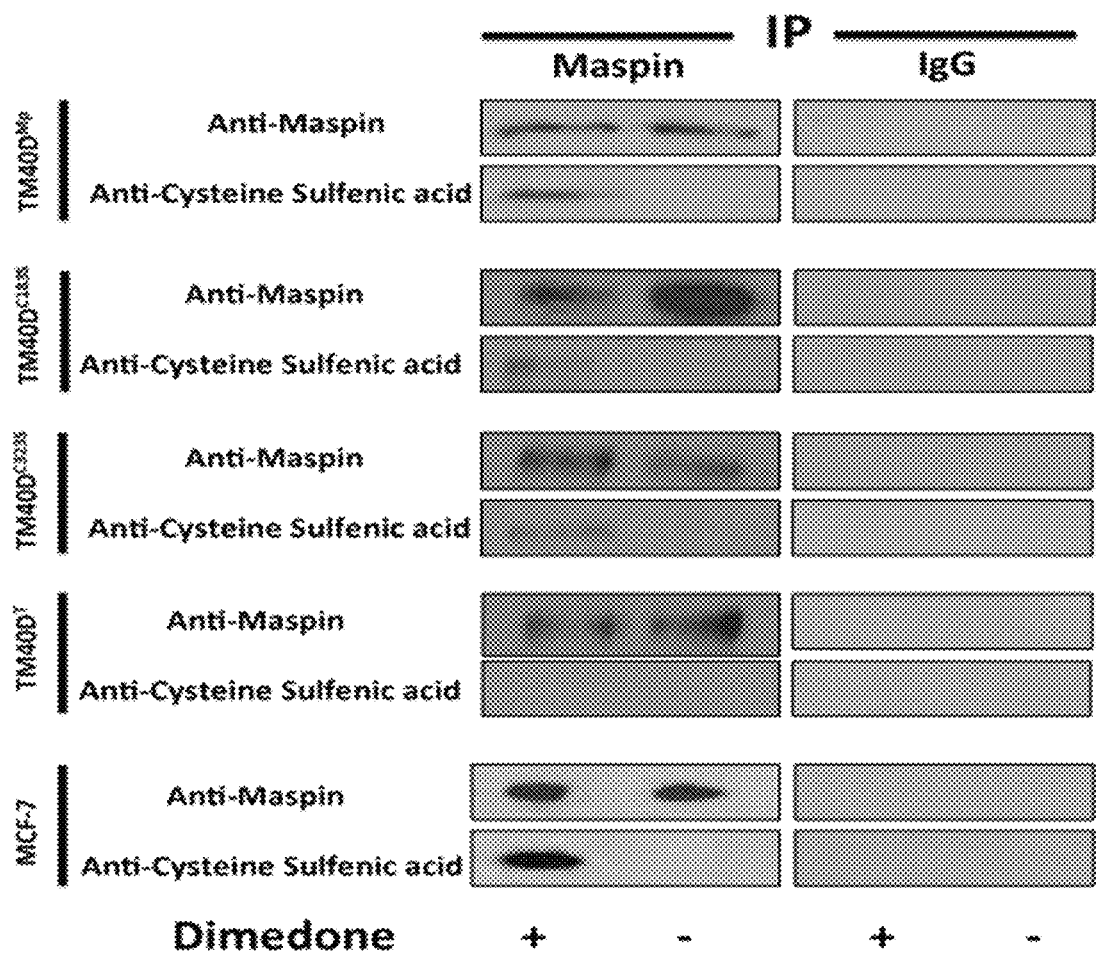

Moreover, to prove the participation of cysteine residues in maintaining the redox state in cells, we immunoprecipitated maspin from hydrogen peroxide treated TM40DMp, TM40DC183S, TM40DC323S and TM40DTcells in the presence or absence of dimedone and the IP-products were analyzed for the presence of dimedone derivatized cysteine sulfenic acid residues under non-denaturing conditions. FIG. 4D shows the presence of maspin cysteine sulfenic acid in TM40DMp, TM40DC183S and TM40DC323S cells but not in the TM40DT cells. These results further demonstrate importance of structurally exposed cysteine residues. Similar results were obtained when the experiment was performed with human mammary cancer epithelial MCF-7 cells (FIG. 4D, bottom panel), which constitutively expresses maspin.

Figure 5B:
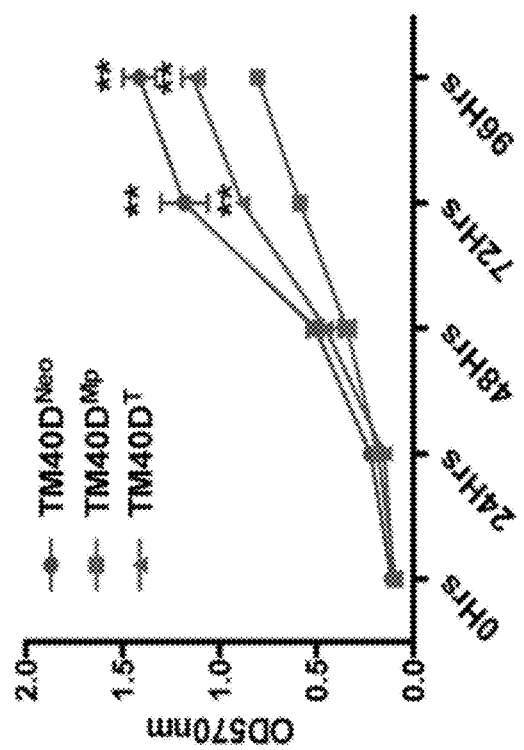
FIGS. 5A-E. Cysteine mutated cells have increased cellular proliferation and ERK1/2 activation. (A) Number of colonies formed in vitro using a soft agar colony formation assay by different cell lines. (B) Comparison of cellular proliferation pattern as determined by MTT assay in three different cell lines. (C) Treatment with anti-oxidant (i.e. NAC) significantly decreases the proliferation in TM40DNeo and TM40DT cells. (D) Comparison of pERK1/2 levels in TM40DNeo and TM40DT cells compared with TM40DMp cells. (E) Effect of NAC treatment on pERK1/2 levels in TM40DNeo, TM40DMp and TM40DT cell. Representative Western blots are shown above the bar diagrams and each lane corresponds to respective bars. Data shown are mean+SD of three independent experiments. Asterisks indicate significance according to t-test (two-tailed); $p<0.01$, *$p<0.001$ FIG. 6. Maspin interacts with Trx-1 in redox regulation. FLAG-Trx-1 was immunoprecipitated from cell lysates of MCF-7-Flag-Trx-C35S cells and analyzed for co-immunoprecipitation of maspin. IgG served as negative control. Input corresponds to the cell lysates before Immunoprecipitation. Top: immunoblot with an anti-maspin rabbit polyclonal antibody; bottom: immunoblot with an anti-FLAG antibody. LC=Light chain, HC=Heavy Chain.
Figure 5A:
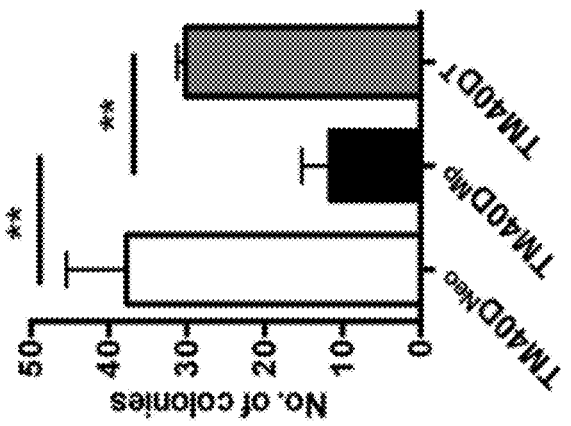
Figure 5C:
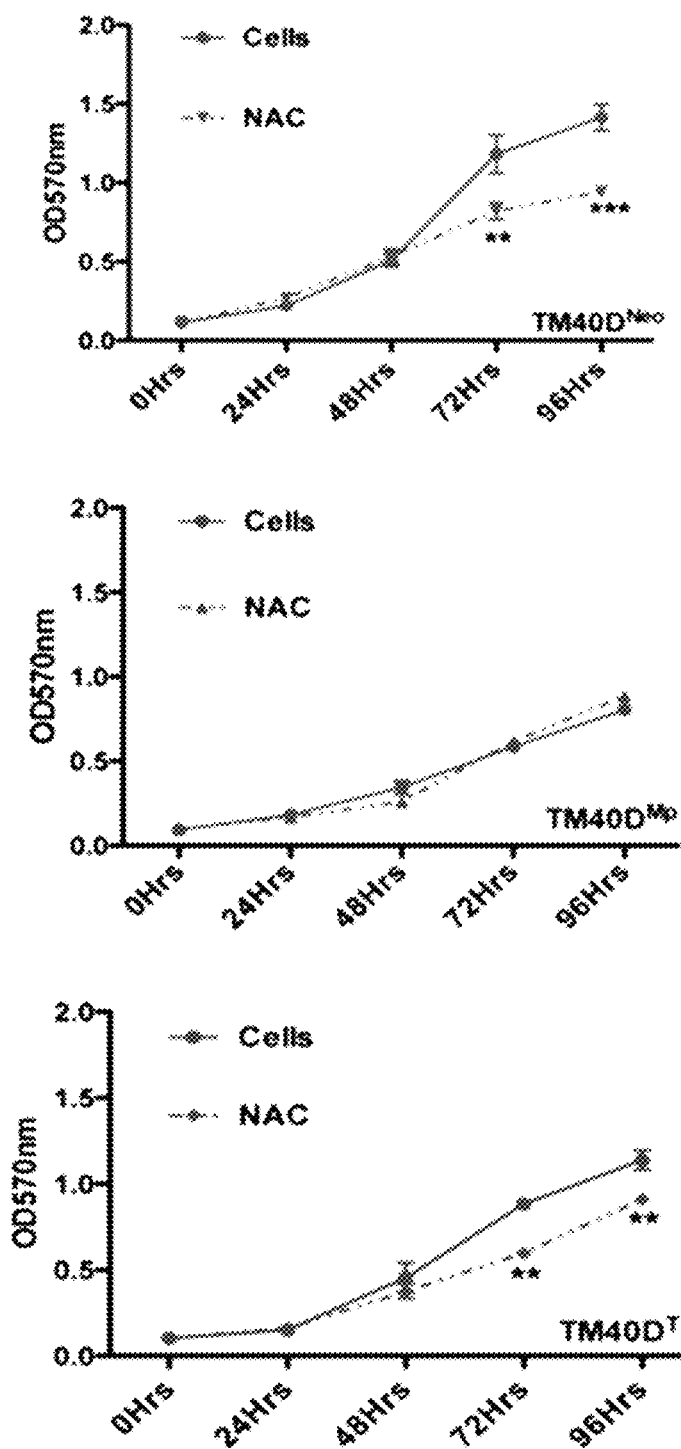
Figure 5D:
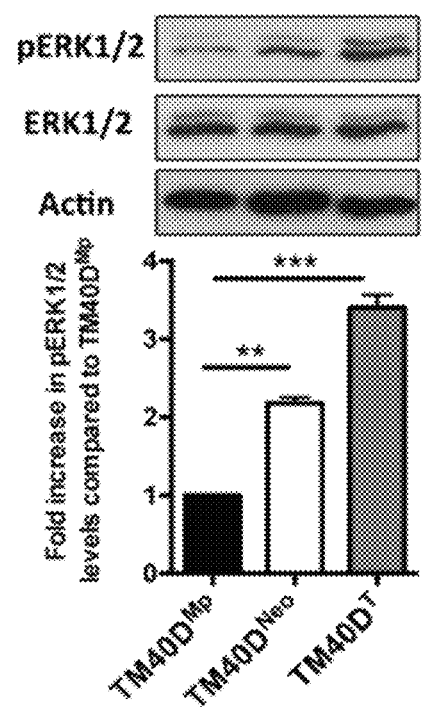

Cysteine residues affect cell proliferation pattern of TM40D cells via activation of ERK1/2—Previously, we and others have shown that maspin suppresses tumor growth, invasion and metastasis of breast and prostate cancer (35, 36). To determine the effect of overexpression of maspin and cysteine mutations on the tumorigenic properties of TM40D cells, we assessed the anchorage independent growth and in vitro proliferation in maspin WT and mutant TM40D cells using soft agar colony formation and MTT assays respectively. Anchorage-independent growth is one of the hallmarks of transformation and soft agar assay is a commonly used in vitro assay for detecting malignant transformation of cells (28,37) The abilities of the cells to form colonies on soft agar are shown in FIG. 5A. Compared with the vector transfected cells, maspin overexpressed TM40DMp cells formed significantly fewer colonies/well ($p<0.01$; FIG. 5A), a feature indicative of decrease in anchorage-independent growth, whereas no significant difference was observed when vector control was compared with the triple mutated maspin ($p>0.05$). A significant increase was observed in the colony formation between TM40DMp and TM40DT cells ($p<0.01$). Results of MTT proliferation assay revealed that WT maspin overexpressing TM40DMp cells have low proliferation rate when compared with TM40DNeo and TM40DT cells over a time period of 96 hrs (FIG. 5B). To obtain direct evidence that deviation in proliferation pattern in TM40DNeo and TM40DT cells is due to changed ROS levels, we treated both types of cells with N-acetyl cysteine (NAC; a strong antioxidant). We observed a significant drop in proliferation rate of TM40DNeo and TM40DT cells with the NAC treatment, whereas, no significant change was observed in TM40DMp cells (FIG. 5C). Thus these results provide strong evidence linking a high proliferation rate to elevated intracellular ROS levels. Increased oxidative stress has been shown to cause proliferation defects in cells via targeting key signaling molecules like ERK1/2 (38). The total ERK1/2 MAP kinase level was found to be nearly constant in all three cell lines derived from TM40D by Western blot analysis (FIG. 5D). However, the corresponding phosphorylated activated forms (p-ERK1/2) were found to be consistently increased in TM40DNeo and TM40DT cells as compared to TM40DMp cells suggesting that TM40DNeo and TM40DT cells have higher constitutive expression of activated pERK1/2 than TM40DMp cells (FIG. 5D). Treating cells with the anti-oxidant NAC significantly reduced the levels of activated pERK1/2 (FIG. 5E) and cell proliferation rate in TM40DNeo and TM40DT cells, however, no change was observed in TM40DMp. These results, clearly demonstrate that maspin inhibits ERK1/2 activities, likely through ROS scavenging and this mechanism controls the epithelial cell proliferation.

Discussion

Oxidative damage to any cellular constituent, if remained unchecked, can lead to disease development (1, 39). Maspin belongs to the serpin family of non-inhibitory protease inhibitor (3) and is abundantly produced in normal mammary luminal epithelial and myoepithelial cells (3, 40). Our laboratory and others have demonstrated maspin acts as a multifaceted protein, interacting with extra- and intracellular groups of proteins and regulating key functions of cell adhesion, motility, apoptosis, and angiogenesis. It is also critical in mammary gland development (4, 18, 41). Role of maspin in oxidative stress has been speculated in the last few years (9, 11). In the present study, we provide evidence for oxidation of cysteine residues in maspin for the first time. Additionally, we demonstrate that maspin acts as a ROS scavenger to provide resistance against oxidative stress. This suggests a new paradigm that maspin allows tumor cells to proliferate in an environment of oxidative stress by maintaining redox homeostasis. Our data also shows that surface-exposed cysteines regulate ROS as an intracellular serpin. Results of adhesion assay (FIG. 4A) clearly demonstrate that this function of ROS regulation is independent of maspin's extracellular function, which increases cell adhesion to ECM matrix when maspin is secreted.

Our results (FIG. 1) indicate that cells expressing maspin have low levels of ROS due to the active participation of maspin in scavenging oxidants. The coordinated action of various cellular anti-oxidants in mammalian cells is critical for maintaining a steady redox state. Also, evidence suggests that maspin expression is regulated in response to redox status. Overexpression of MnSOD leads to an increased maspin expression (42,43). This reinforces involvement of maspin in the regulation of cellular redox homeostasis.

We tested whether maspin expression level in normal mammary epithelial cells or in cells with reduced level of maspin (e.g. MCF-10A229) regulates cellular redox status. We then reintroduced maspin into tumor cells that do not express maspin, to study the mechanism of maspin-mediated regulation of cellular ROS. A reduction in total intracellular ROS (FIG. 2B) in maspin overexpressing mouse mammary epithelial cell (TM40D) further substantiates the importance of maspin in maintaining the redox state of cells. Increasing ROS in the mitochondria (antimycin-A treatment) shows the physiological relevance (FIG. 2C) of maspin in oxidative stress, which is consistent with our finding that maspin attenuates ROS species such as superoxide ($O_2^{\circ}-$) in STS-stressed TM40D cells (FIG. 2E). Taken together, our results indicate that presence of maspin in mammary cells make them more efficient to fight against ROS irrespective of their origins; whether they are derived from mouse tumor epithelial cell (TM40D), or primary mouse epithelial cells, or human mammary epithelial MCF-10A cells. Emerging evidence suggests that redox-sensitive cysteine residues in proteins may function as an oxidant sensor (44,45). The conversion of these residues to sulfenic acid has been demonstrated for redox signaling in yeast, T-cell activation, and in other proteins (14,15,45), providing strong support for the growing roles of this modification in biology. Mutating three cysteine residues in maspin resulted in significant increase in intracellular ROS levels in TM40DT cells (FIG. 3C). Further, levels of other anti-oxidant proteins were also found to alter in cells expressing cysteine to serine mutant maspin (TM40DT) when compared with the WT maspin expressing cells (TM40DMp). Our data suggests that these cysteines have a cumulative effect because mutation of either C183S or C323S led to similar significant increase in cellular ROS level. The cells with triple mutations in maspin had ~1.4 fold increase in ROS level than cells with single cysteine mutation (FIG. 3C). However, while not limiting the present invention, it is possible that certain redox agents may preferentially attack a particular cysteine on maspin in vivo depending on their size and structure.

Figure 5E:
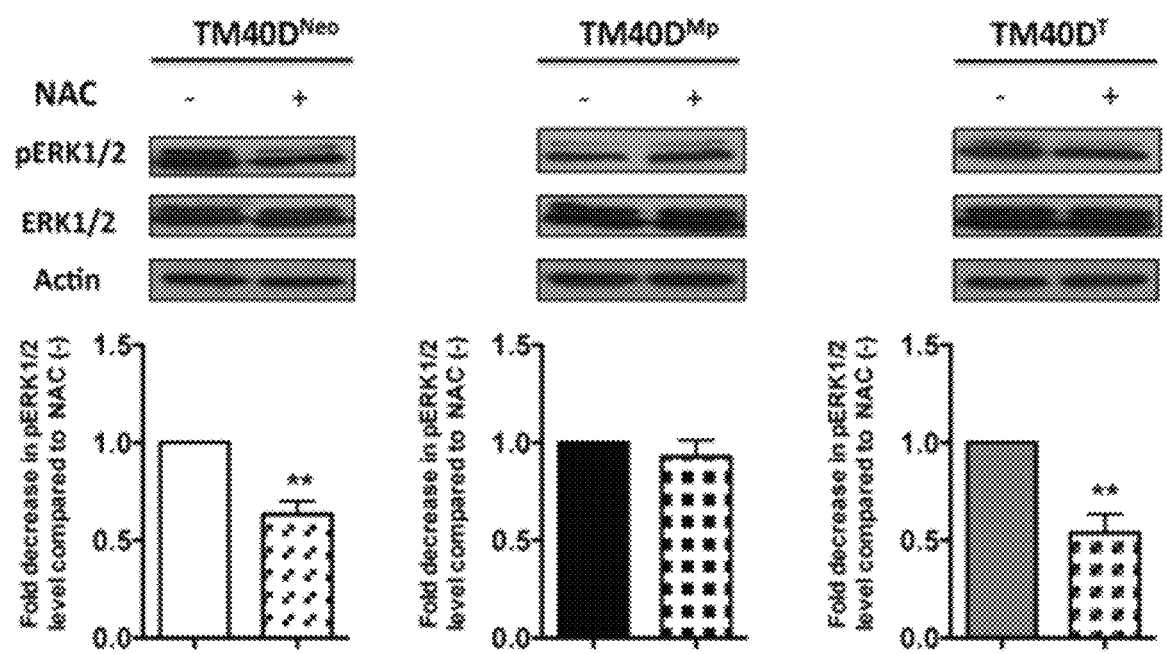

Besides its importance in redox homeostasis, overexpression of maspin also inhibits cancer cell proliferation. Maspin overexpressing cells have reduced capacities to form colonies and to grow in soft agar. Mutation of cysteine residues resulted in a phenotype, which forms more colonies (FIG. 5A). Results of MTT assay revealed that TM40DNeo cells proliferate more rapidly than WT maspin overexpressing cells. Increased proliferation of TM40DNeo cells coincides with the increased ROS levels in these cells (FIGS. 2B and 5B). Cells with mutated maspin (TM40DT) also proliferate more rapidly when compared to TM40DMp cells (FIG. 5B). In agreement with this, Cia et al have also reported decreased proliferation rate with the maspin overexpression in esophageal carcinoma (46). Also, NAC treatment reversed the oxidative stress phenotype of the maspin deficient or mutated maspin cells and thus indicating proliferation was a result of increased ROS in these cells. ROS can activate kinases and/or inhibit phosphatases resulting in stimulation of signaling pathways such as ERK1/2 (mitogen activated protein kinases) that are important in cell proliferation, differentiation, invasion, and apoptosis (47). In the present study, we found higher levels of phospho-ERK1/2 in TM40DNeo and TM40DT cells as compared with TM40DMp cells (FIG. 5D). Anti-oxidant pre-treatment led to a decrease in expression of pERK1/2 in these cells (FIG. 5E). These observations suggest that an increased oxidative stress activates ERK1/2, which in turn increases proliferation. These results collectively substantiate that maspin overexpressing cells have lower ROS and therefore maintain lower levels of pERK1/2 and proliferation rates, as compared with cell lines that have attenuated or mutated maspin expression.

This study indicates that under oxidative stress, cysteine thiols [—SH] in maspin are oxidized to cysteine sulfenic acid [—SOH], which may further interact with GST (9) or some other unidentified molecule(s) which reduces the oxidized thiol in the cells (e.g. glutathione, peroxiredoxin etc). Reducing—SOH to —SH in maspin makes it available for recycling and for scavenging more ROS in the intracellular microenvironment. Increased oxidative stress in cells with triple mutated maspin demonstrates the absence of above proposed mechanism. Cells expressing WT maspin have low proliferation rate, which is attributed to the low ROS levels, and therefore, suppressed tumor growth. In conclusion, maspin overexpression leads to resistance against oxidative stress and maspin cysteine residues play an important role in maintaining the redox status of cells.

Example 2

Maspin Interacts with Trx-1 in Redox Regulation

Figure 6:
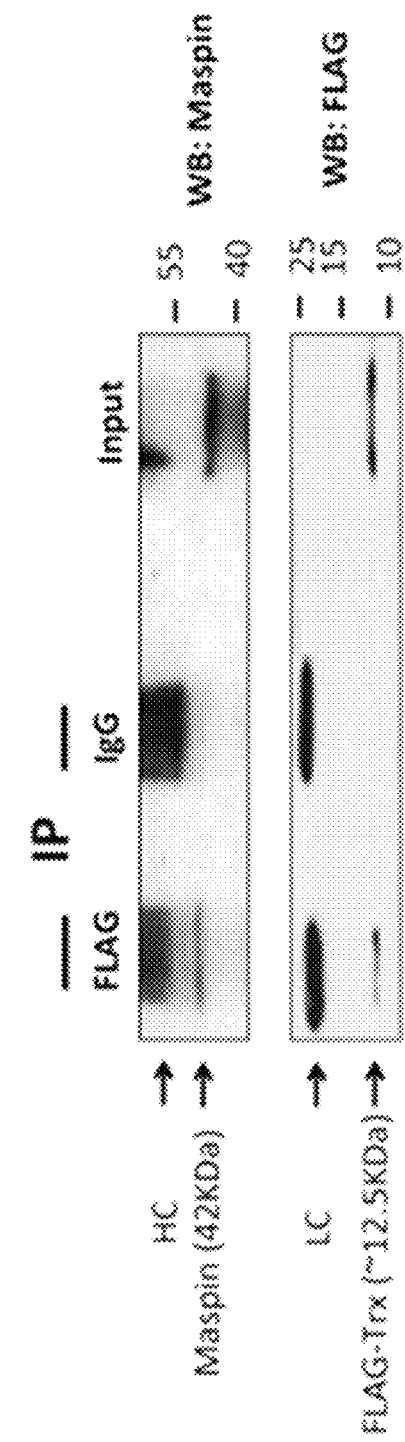

Maspin displays a conformational change from open to closed status around the G-helix region (Law et al., J Biol Chem (2005), herein incorporated by reference). Three structurally close cysteines in maspin protein (C20, and C287 or C373) are exposed in opened conformation, which are subject to ROS attacks and form disulfide bond within maspin molecule. In fact, we had previously observed the formation of maspin intramolecular disulfide bonds in human breast epithelial MCF10A cells (Nawata, et al., Int J Mol Med 27, 249-54 (2011), herein incorporated by reference). In biological systems, cytoplasmic disulfide bonds are generally taken care of by Trx1 (Nakamura et al, Antioxid Redox Signal 7, 823-8 (2005), herein incorporated by reference). To determine whether maspin disulfide bond interacts with Trx1, we first transfected flag-tagged cysteine mutated Trx1 (cysteine C35 is mutated to alanine) to the maspin-expressing MCF7 breast tumor cells and established stable transfectants. The mutant Trx1-C35A allows us to probe maspin-Trx1 interaction because the intermediate complex between maspin and the Trx1-C35A is stable in cells. We exposed stable cloned cells with $H_2O_2$ at 250 µM for 3 hours, harvested cell extracts for immunoprecipitation with anti-flag antibody, and followed with Western blot analysis using anti-maspin antibody. Our data showed that maspin indeed interacts with Trx1 in MCF-7 cells (FIG. 6). Recently, we identified cysteine 20 as the key residue involved in maspin interaction with Trx1. It forms a disulfide bond with the adjacent cysteine 287 or cysteine 373, promoting maspin protein to undergo a structural change to the closed conformation upon ROS attack. The closed conformation will likely change back to the open conformation through reduction reaction with Trx1. This new discovery, together with our previous findings that maspin uses its three cysteines to control ROS, explain why maspin is such a powerful anti-ROS scavenger against inflammation, cancer, and aging in various cells and tissues.

REFERENCES

1. Weinberg, F., and Chandel, N. S. (2009) Cell Mol Life Sci 66, 3663-3673
2. Khandrika, L., Kumar, B., Koul, S., Maroni, P., and Koul, H. K. (2009) Cancer Lett 282, 125-136
3. Zou, Z., Anisowicz, A., Hendrix, M. J., Thor, A., Neveu, M., Sheng, S., Rafidi, K., Seftor, E., and Sager, R. (1994) Science 263, 526-529
4. Zhang, M., Volpert, O., Shi, Y. H., and Bouck, N. (2000) Nat Med 6, 196-199
5. Endsley, M. P., Hu, Y., Deng, Y., He, X., Warejcka, D. J., Twining, S. S., Gonias, S. L., and Zhang, M. (2011) The Journal of biological chemistry 286, 24599-24607
6. Qin, L., and Zhang, M. (2010) The Journal of biological chemistry 285, 32360-32369
7. Bodenstine, T. M., Seftor, R. E., Khalkhali-Ellis, Z., Seftor, E. A., Pemberton, P. A., and Hendrix, M. J. (2012) Cancer metastasis reviews 31, 529-551
8. Jiang, N., Meng, Y., Zhang, S., Mensah-Osman, E., and Sheng, S. (2002) Oncogene 21, 4089-4098
9. Yin, S., Li, X., Meng, Y., Finley, R. L., Jr., Sakr, W., Yang, H., Reddy, N., and Sheng, S. (2005) The Journal of biological chemistry 280, 34985-34996
10. Bailey, C. M., Khalkhali-Ellis, Z., Kondo, S., Margaryan, N. V., Seftor, R. E., Wheaton, W. W., Amir, S., Pins, M. R., Schutte, B. C., and Hendrix, M. J. (2005) The Journal of biological chemistry 280, 34210-34217
11. Nawata, S., Shi, H. Y., Sugino, N., and Zhang, M. (2011) Int J Mol Med 27, 249-254
12. Poole, L. B., Karplus, P. A., and Claiborne, A. (2004) Annu Rev Pharmacol Toxicol 44, 325-347
13. Poole, L. B., and Nelson, K. J. (2008) Curr Opin Chem Biol 12, 18-24
14. Nelson, K. J., Klomsiri, C., Codreanu, S. G., Soito, L., Liebler, D. C., Rogers, L. C., Daniel, L. W., and Poole, L. B. (2010) Methods Enzymol 473, 95-115
15. Klomsiri, C., Nelson, K. J., Bechtold, E., Soito, L., Johnson, L. C., Lowther, W. T., Ryu, S. E., King, S. B., Furdui, C. M., and Poole, L. B. (2010) Methods Enzymol 473, 77-94
16. Law, R. H., Irving, J. A., Buckle, A. M., Ruzyla, K., Buzza, M., Bashtannyk-Puhalovich, T. A., Beddoe, T. C., Nguyen, K., Worrall, D. M., Bottomley, S. P., Bird, P. I., Rossjohn, J., and Whisstock, J. C. (2005) The Journal of biological chemistry 280,
17. Al-Ayyoubi, M., Gettins, P. G., and Volz, K. (2004) The Journal of biological chemistry 279, 55540-55544
18. Zhang, W., Shi, H. Y., and Zhang, M. (2005) BMC Cancer 5, 50
19. Shi, H. Y., Stafford, L. J., Liu, Z., Liu, M., and Zhang, M. (2007) Cell Motil Cytoskeleton 64, 338-346
20. Gao, F., Shi, H. Y., Daughty, C., Cella, N., and Zhang, M. (2004) Development 131, 1479-1489
21. Danielson, K. G., Oborn, C. J., Durban, E. M., Butel, J. S., and Medina, D. (1984) Proceedings of the National Academy of Sciences of the United States of America 81, 3756-3760

22. Eruslanov, E., and Kusmartsev, S. (2010) Methods Mol Biol 594, 57-72
23. Zielonka, J., and Kalyanaraman, B. (2010) Free Radic Biol Med 48, 983-1001
24. Pong, K., Doctrow, S. R., Huffman, K., Adinolfi, C. A., and Baudry, M. (2001) Exp Neurol 171, 84-97
25. Krohn, A. J., Preis, E., and Prehn, J. H. (1998) J Neurosci 18, 8186-8197
26. Corbett, S. A., Wilson, C. L., and Schwarzbauer, J. E. (1996) Blood 88, 158-166
27. Charles, R. L., Schroder, E., May, G., Free, P., Gaffney, P. R., Wait, R., Begum, S., Heads, R. J., and Eaton, P. (2007) Molecular & cellular proteomics: MCP 6, 1473-1484
28. Sabherwal, Y., Mahajan, N., Helseth, D. L., Gassmann, M., Shi, H., and Zhang, M. (2012) International journal of oncology 40, 1889-1899
29. Aghajanian, A., Wittchen, E. S., Campbell, S. L., and Burridge, K. (2009) PloS one 4, e8045
30. Hoffman, D. L., and Brookes, P. S. (2009) The Journal of biological chemistry 284, 16236-16245
31. Kulinskii, V. I., and Kolesnichenko, L. S. (2009) Biomeditsinskaia khimiia 55, 255-277
32. Xiao, G. G., Wang, M., Li, N., Loo, J. A., and Nel, A. E. (2003) The Journal of biological chemistry 278, 50781-50790
33. Serru, V., Baudin, B., Ziegler, F., David, J. P., Cals, M. J., Vaubourdolle, M., and Mario, N. (2001) Clinical chemistry 47, 1321-1324
34. Cella, N., Contreras, A., Latha, K., Rosen, J. M., and Zhang, M. (2006) FASEB J 20, 1510-1512
35. Shi, H. Y., Zhang, W., Liang, R., Abraham, S., Kittrell, F. S., Medina, D., and Zhang, M. (2001) Cancer research 61, 6945-6951
36. Li, Z., Shi, H. Y., and Zhang, M. (2005) Oncogene 24, 2008-2019
37. Schaefer, J. S., Sabherwal, Y., Shi, H. Y., Sriraman, V., Richards, J., Minella, A., Turner, D. P., Watson, D. K., and Zhang, M. (2010) The Journal of biological chemistry 285, 11258-11269
38. Brown, M. D., and Sacks, D. B. (2009) Cell Signal 21, 462-469
39. Dalle-Donne, I., Rossi, R., Colombo, R., Giustarini, D., and Milzani, A. (2006) Clinical chemistry 52, 601-623
40. Reddy, K. B., McGowen, R., Schuger, L., Visscher, D., and Sheng, S. (2001) Oncogene 20, 6538-6543
41. Bailey, C. M., Khalkhali-Ellis, Z., Seftor, E. A., and Hendrix, M. J. (2006) Journal of cellular physiology 209, 617-624
42. Duan, H., Zhang, H. J., Yang, J. Q., Oberley, L. W., Futscher, B. W., and Domann, F. E. (2003) Antioxidants & redox signaling 5, 677-688
43. Li, J. J., Colburn, N. H., and Oberley, L. W. (1998) Carcinogenesis 19, 833-839
44. Wang, Y., Yang, J., and Yi, J. (2012) Antioxidants & redox signaling 16, 649-657
45. Seo, Y. H., and Carroll, K. S. (2009) Proceedings of the National Academy of Sciences of the United States of America 106, 16163-16168
46. Cai, Z., Zhou, Y., Lei, T., Chiu, J. F., and He, Q. Y. (2009) Cancer 115, 36-48
47. Meng, T. C., Fukada, T., and Tonks, N. K. (2002) Mol Cell 9, 387-399

All publications and patents mentioned in the present application are herein incorporated by reference. Various modification and variation of the described methods and compositions of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that are obvious to those skilled in the relevant fields are intended to be within the scope of the following claims.

I claim:

1. A method of reducing skin wrinkles in a human subject in need thereof, wherein the method comprises:
   administering to an area of the skin comprising wrinkles a composition comprising
   a derivative of human maspin comprising any one of: SEQ ID NOS: 9, 10, 11, and 12; and wherein said composition is in the form of cream, lotion, spray, ointment, gel, powdered mask, paste, cleanser, foundation, salve or tincture.

2. The method of claim 1, wherein said area of skin is a portion of said human subject's face.

3. The method of claim 2, wherein said portion of said human subject's face is around eyes.

4. The method of claim 2, wherein said portion of said human subject's face is around mouth.

5. The method of claim 1, wherein said human subject is at least 50 years old.

6. The method of claim 1, wherein said human subject is at least 60 years old.

7. The method of claim 1, wherein said human subject is at least 70 years old.

8. The method of claim 1, wherein said human subject is at least 80 years old.

9. The method of claim 1, wherein said human subject is at least 90 years old.

10. The method of claim 1, wherein said composition is in the form of cream.

11. The method of claim 1, wherein said composition is in the form of lotion.

12. The method of claim 1, wherein said composition is in the form of spray.

13. The method of claim 1, wherein said composition is in the form of ointment.

14. The method of claim 1, wherein said composition is in the form of gel.

15. The method of claim 1, wherein said composition is in the form of powdered mask.

16. The method of claim 1, wherein said composition is in the form of paste.

17. The method of claim 1, wherein said composition is in the form of cleanser.

18. The method of claim 1, wherein said composition is in the form of foundation.

19. The method of claim 1, wherein said composition is in the form of salve.

20. The method of claim 1, wherein said composition is in the form of tincture.

\* \* \* \* \*